United States Patent
Lomas et al.

(10) Patent No.: US 12,142,363 B2
(45) Date of Patent: *Nov. 12, 2024

(54) GENETICALLY PERSONALIZED FOOD RECOMMENDATION SYSTEMS AND METHODS

(71) Applicant: REVIV GLOBAL LTD, Knutsford (GB)

(72) Inventors: Sarah Lomas, Cheshire (GB); Michael Barnish, Cheshire (GB); Johnny Parvani, Phoenix, AZ (US)

(73) Assignee: REVIV GLOBAL LTD

( * ) Notice: Subject to any disclaimer, the term of this patent is extended or adjusted under 35 U.S.C. 154(b) by 0 days.

This patent is subject to a terminal disclaimer.

(21) Appl. No.: 18/116,933

(22) Filed: Mar. 3, 2023

(65) Prior Publication Data

US 2023/0207102 A1 Jun. 29, 2023

Related U.S. Application Data

(63) Continuation of application No. 17/876,383, filed on Jul. 28, 2022, now Pat. No. 11,600,375.

(Continued)

(51) Int. Cl.
G16H 20/60 (2018.01)

(52) U.S. Cl.
CPC ................... *G16H 20/60* (2018.01)

(58) Field of Classification Search
CPC ............................. G16H 20/00; G16H 20/60
See application file for complete search history.

(56) References Cited

U.S. PATENT DOCUMENTS 8,560,334 B2 10/2013 Laehteenmaeki
10,929,916 B2 2/2021 Abutair
(Continued)

FOREIGN PATENT DOCUMENTS

CA 3014239 2/2020
CN 106326683 1/2017
(Continued)

OTHER PUBLICATIONS

Verkaik-Kloosterman, Janneke; Estimation of Micronutrient Intake Distributions: Development of Methods to Support Food and Nutrition Policy Making; Wageningen University and Research, ProQuest Dissertations & Theses, 2011. 28235724. (Year: 2011).*

(Continued)

*Primary Examiner* — Hiep V Nguyen
(74) *Attorney, Agent, or Firm* — Booth Udall Fuller, PLC; Kenneth C. Booth

(57) ABSTRACT

A method of providing genetically personalized food recommendations includes storing, in a food micronutrient database accessible through an electronic device, a mapping of individual micronutrients to genetic information, medical information, and therapeutic objectives, a food menu for at least one restaurant, and nutrient data of each menu item on the food menu. The method also includes receiving and storing genetic information, medical information, therapeutic objectives, and dietary preferences of a user. The method also includes receiving input from the user indicating a restaurant where the user plans to eat food, identifying micronutrient(s) that match the genetic information, the medical information, and the therapeutic objectives of the user based on the mapping, identifying menu items that provide the micronutrient(s) and align with the dietary preferences of the user; and outputting to the user a person- (Continued)

alized list of food choices at the restaurant that are healthiest for the user.

20 Claims, 9 Drawing Sheets

Related U.S. Application Data

(60) Provisional application No. 63/227,952, filed on Jul. 30, 2021.

(56) References Cited

U.S. PATENT DOCUMENTS

| | | | |
|---|---|---|---|
| 2002/0058712 | A1 | 5/2002 | Sneed |
| 2005/0177397 | A1 | 8/2005 | Kane |
| 2006/0062859 | A1 | 3/2006 | Blum |
| 2006/0199155 | A1 | 9/2006 | Mosher |
| 2007/0154498 | A1 | 7/2007 | Bortz |
| 2008/0050740 | A1 | 2/2008 | Cassidy |
| 2008/0221932 | A1 | 9/2008 | Kane |
| 2009/0155381 | A1 | 6/2009 | Goralczyc |
| 2009/0192365 | A1 | 7/2009 | Gisel |
| 2011/0113002 | A1 | 5/2011 | Kane |
| 2011/0189161 | A1 | 8/2011 | Blum |
| 2012/0083669 | A1 | 4/2012 | Abujbara |
| 2012/0290327 | A1 | 11/2012 | Hanlon |
| 2013/0018024 | A1 | 1/2013 | Bianchi |
| 2013/0216982 | A1 * | 8/2013 | Bennett .............. A61B 5/4866 434/127 |
| 2014/0052722 | A1 | 2/2014 | Bertsimas |
| 2014/0088995 | A1 | 3/2014 | Damani |
| 2015/0125462 | A1 | 5/2015 | Bek |
| 2015/0269865 | A1 | 9/2015 | Volach |
| 2018/0032682 | A1 | 2/2018 | Donalds |
| 2018/0039759 | A1 | 2/2018 | Astigarraga |
| 2018/0089385 | A1 | 3/2018 | Gupta |
| 2018/0121631 | A1 | 5/2018 | Mehta |
| 2018/0144820 | A1 | 5/2018 | Grimmer |
| 2018/0353425 | A1 | 12/2018 | Narain |
| 2018/0374567 | A1 | 12/2018 | Toumazou |
| 2019/0152663 | A1 | 5/2019 | Kraft |
| 2019/0221303 | A1 | 7/2019 | Bennett |
| 2019/0290172 | A1 | 9/2019 | Hadad |
| 2020/0135314 | A1 | 4/2020 | Gostyla |
| 2021/0005304 | A1 | 1/2021 | Neumann |
| 2021/0005317 | A1 | 1/2021 | Neumann |
| 2021/0012880 | A1 | 1/2021 | Ando |
| 2021/0050086 | A1 | 2/2021 | Rose |
| 2021/0134434 | A1 | 5/2021 | Riley |
| 2021/0166794 | A1 | 6/2021 | Nova |
| 2021/0193332 | A1 | 6/2021 | Inwald |

FOREIGN PATENT DOCUMENTS

| | | | |
|---|---|---|---|
| CN | 112069382 | 12/2020 | |
| EP | 3529379 B1 * | 5/2022 | ............. A23L 33/30 |
| KR | 20170054628 | 5/2017 | |
| KR | 102043959 | 11/2019 | |
| KR | 20190138360 | 12/2019 | |
| KR | 102169661 | 10/2020 | |
| KR | 20210061032 | 5/2021 | |
| KR | 20210072221 | 6/2021 | |
| KR | 102278646 | 7/2021 | |
| WO | 2004084822 | 10/2004 | |
| WO | 2012067525 | 5/2012 | |
| WO | 2013086582 | 6/2013 | |
| WO | 2015004266 | 1/2015 | |
| WO | 2019183404 | 9/2019 | |
| WO | WO-2019183404 A1 * | 9/2019 | ........... A61B 5/0022 |
| WO | 2020138720 | 7/2020 | |

OTHER PUBLICATIONS

Chen, Yu et al. Personalized Food Recommendation as Constrained Question Answering over a Large-scale Food Knowledge Graph. Rensselaer Polytechnic Institute, Troy, NY. 2021. 9 pages.

Drabsch, T. et al. A Scientific Perspective of Personalised Gene-Based Dietary Recommendations for Weight Management. Nutrients. 2019, 14 pages.

Galyean, S. et al., 'Personalized Nutrition for Management of Micronutrient Deficiency—Literature Review in Non-bariatric Populationsand Possible Utility in Bariatric Cohort', Obesity Surgery, 2020, vol. 30, pp. 3570-3582.

Ingilizian, Z. How Precision Consumption Can Improve Consumer Health and Well-Being. Forbes. Leadership Strategy. 2020, 7 pages.

Lubos, E. et al. Glutathione Peroxidase-1 in Health and Disease: From Molecular Mechanisms to Therapeutic Opportunities. Antioxid Redox Signal. 2011, 42 pages.

Morine, M. J. et al., 'Genetic associations with micronutrient levels identified in immune and gastrointestinal networks', Genes Nutr., 2014, vol. 9, No. 408, pp. 1-19.

NutriGenomeDB platform, 1 page, http://www.nutrigenomedb.org/.

Precision Consumer 2030 when data becomes invisible. Sparks & Honey. Culture Forecast. 2019, 125 pages.

Verkaik-Kloosterman, Janneke; Estimation of Micronutrient Intake Distributions: Development of Methods to Support Food and Nutrition Policy Making; Wageningen University and Research. ProQuest Dissertations Publishing, 2011. 28235724. (Year: 2011) 192 pages.

Berthon et al., "Nutrition and Respiratory Health-Feature Review", Mar. 5, 2015, Nutrients, vol. 7, 1618-1643. (Year: 2015).

Brouwer ID et al: "Reverse thinking: taking a healthy diet perspective towards food systems transformations", Food Security, Springer Netherlands, Dordrecht, vol. 13, No. 6, Oct. 16, 2021 (Oct. 16, 2021), pp. 1497-1523, XP037646513, ISSN: 1876-4517, DOI: 10.1007/SI2571-021-01204-5 [retrieved on Oct. 16, 2021].

Bujari Armir et al: "A mobile sensing and visualization platform for environmental data", Pervasive and Mobile Computing, Elsevier, NL, vol. 66, Jun. 18, 2020 (Jun. 18, 2020), XP086246547, ISSN: 1574-1192, DOI: 10.1016/J.PMCJ.2020.101204 [retrieved on Jun. 18, 2020].

Maestre Mar et al: "Assessing food value chain pathways, linkages and impacts for better nutrition of vulnerable groups", Food Policy, Pergamon, Amsterdam, NL, vol. 68, Jan. 11, 2017 (Jan. 11, 2017), pp. 31-39, XP029956443, ISSN: 0306-9192, DOI: 10.1016/J.FOODPOL.2016.12.007 p. 31-p. 36; figure 1.

Matthew Metzgar et al: "The feasibility of a Paleolithic diet for low-income consumers", Nutrition Research, Elsevier, Amsterdam, NL, vol. 31, No. 6, May 14, 2011 (May 14, 2011), pp. 444-451, XP028379237, ISSN: 0271-5317, DOI: 10.1016/J.NUTRES.2011.05.008 [retrieved on May 23, 2011].

Poole Nigel et al: "Viewpoint: Agri-nutrition research: Revisiting the contribution of maize and wheat to human nutrition and health", Food Policy, Pergamon, Amsterdam, NL, vol. 100, Sep. 18, 2020 (Sep. 18, 2020), XP086547134, ISSN: 0306-9192, DOI: 10.1016/J.FOODPOL.2020.101976 [retrieved on Sep. 18, 2020].

William A Masters et al: "The economics of malnutrition: Dietary transition and food system transformation", arxiv.org, Cornell University Library, 201 Olin Library Cornell University Ithaca, NY 14853, Feb. 5, 2022 (Feb. 5, 2022), XP091150658, abstract; table 1 p. 97.

* cited by examiner

| | | | | $M_1$ | $M_2$ |
|---|---|---|---|---|---|
| SNP$_1$ | S$_1$ | C$_1$ | TO$_1$ | ✓ | |
| | | | TO$_2$ | | ✓ |
| | | C$_2$ | TO$_1$ | ✓ | |
| | | | TO$_2$ | | ✓ |
| | S$_2$ | C$_1$ | TO$_1$ | ✓ | |
| | | | TO$_2$ | | ✓ |
| | | C$_2$ | TO$_1$ | ✓ | |
| | | | TO$_2$ | | ✓ |
| SNP$_2$ | S$_1$ | C$_1$ | TO$_1$ | | ✓ |
| | | | TO$_2$ | | ✓ |
| | | C$_2$ | TO$_1$ | ✓ | |
| | | | TO$_2$ | ✓ | |
| | S$_2$ | C$_1$ | TO$_1$ | | ✓ |
| | | | TO$_2$ | | ✓ |
| | | C$_2$ | TO$_1$ | ✓ | |
| | | | TO$_2$ | ✓ | |

FIG. 3

GENETICALLY PERSONALIZED FOOD RECOMMENDATION SYSTEMS AND METHODS

RELATED APPLICATIONS

This application is a continuation of U.S. Utility application Ser. No. 17/876,383, filed Jul. 28, 2022, which application claims the benefit of U.S. Provisional Application No. 63/227,952, filed Jul. 30, 2021, the disclosures of which are hereby incorporated by reference in their entirety.

TECHNICAL FIELD

This disclosure relates generally to food micronutrient databases, and more specifically to a process for personalizing food recommendations based on genetic data. The food recommendations may also or alternatively be personalized based on other medical data, therapeutic objectives and/or dietary preferences.

BACKGROUND

Achieving and maintaining optimal health and proper function of the human body requires proper nutrition and hydration, including a correct balance of nutrients such as macronutrients (e.g., proteins, carbs, fats) and micronutrients (e.g., vitamins, minerals, antioxidants). Food micronutrient databases have been created to aid individuals in understanding the nutrients found in different foods and making decisions about which foods to consume. Different micronutrient databases may suggest different amounts of food for consumption based on the type of food and the nutrients found therein. However, current food micronutrient databases make assumptions about the optimal amounts of nutrients to consume based on broad averages, without looking at the individual's specific needs. Because each individual is unique and has different requirements for nutrients, the recommendations for the general public may not actually correlate to what any specific individual needs. Thus, current food micronutrient databases may suggest foods and amounts of food that could result in excess unnecessary nutrients or omit vital ingredients, compromising the ability of the food micronutrient database to provide recommendations that accurately portray the needs of the individual.

SUMMARY

Aspects of this disclosure relate to a method of providing genetically personalized food recommendations, the method comprising: storing, in a food micronutrient database accessible through an electronic device, a mapping of individual micronutrients to genetic information, medical information, and therapeutic objectives, wherein the mapping comprises genetic modifiers information about how different genes, genotypes, and genomes react to each micronutrient and combination of micronutrients; storing, in the food micronutrient database, a food menu for at least one restaurant and nutrient data of each menu item on the food menu, the nutrient data comprising proximates data, inorganics data, micronutrients data, vitamin fractions data, fatty acid compositions data, and bioactive compounds data; receiving genetic information, medical information, therapeutic objectives, and dietary preferences of a user; storing, in a user library coupled with the food micronutrient database, the genetic information, the medical information, the therapeutic objectives, and the dietary preferences of the user; receiving input from the user through a software application indicating a specific restaurant selected from among the at least one restaurant where the user plans to eat food; identifying one or more micronutrients that match the genetic information, the medical information, and the therapeutic objectives of the user based on the mapping; identifying menu items from the food menu that provide the one or more micronutrients and align with the dietary preferences of the user; and outputting to the user a personalized list of food choices comprising the identified menu items from the food menu of the restaurant that are healthiest options for the user based on the genetic information, the medical information, the therapeutic objectives, and the dietary preferences of the user.

Particular implementations may comprise one or more of the following features. Developing the mapping, the developing the mapping comprising, for each specific micronutrient of the individual micronutrients: creating an individual score for each of a plurality of existing individual scientific literature references that links the specific micronutrient to at least one of specific genetic information, specific medical information, and a specific therapeutic objective; adding the individual scores for each of the plurality of existing individual scientific literature references for the specific micronutrient with respect to each combination of specific genetic information, specific medical information, and the specific therapeutic objective; and determining that the specific micronutrient matches the specific genetic information, the specific medical information, and the specific therapeutic objective when a sum of the individual scores for the specific micronutrient with respect to the specific genetic information, the specific medical information, and the specific therapeutic objective exceeds a predetermined threshold. Administering a genetic test to the user to determine the genetic information of the user. Receiving input from the user indicating the menu items consumed by the user. Receiving feedback data about an effectiveness of the consumed menu items in improving the medical information or in making progress on reaching the therapeutic objectives. Creating an individual food score for the consumed menu items with respect to the genetic information, the medical information, and the therapeutic objectives of the user based on the feedback data; and updating the mapping based on the individual food score; and outputting future recommendations for the user and other users with reference to the updated mapping. Receiving subjective feedback data about how the user enjoyed the consumed menu items; and updating the dietary preferences of the user based on the subjective feedback data. Outputting a list of menu items from the food menu that are worst for the user to consume based on the genetic information, the medical information, and the therapeutic objectives of the user.

Aspects of this disclosure relate to a method of providing genetically personalized food recommendations, the method comprising: storing, in a food micronutrient database, food nutrient data for a plurality of foods and information about nutritional needs associated with a plurality of combinations of genetic information, medical information, and therapeutic objectives, the food nutrient data comprising proximates data, inorganics data, micronutrients data, vitamin fractions data, fatty acid compositions data, and bioactive compounds data; receiving genetic information, medical information, therapeutic objectives, and dietary preferences of a user; storing, in a user library, the genetic information, the medical information, the therapeutic objectives, and the dietary preferences of the user; determining nutritional needs of the user based on the genetic information, the medical information, and the therapeutic objectives of the user and the information about nutritional needs stored in the food micronutrient database associated with the user's combination of genetic information, medical information, and therapeutic objectives; analyzing the food nutrient data of the plurality of foods to identify one or more foods of the plurality of foods that will provide the nutritional needs of the user; comparing the identified one or more foods with the dietary preferences of the user; and outputting a food recommendation to the user that comprises food selected from the identified one or more foods that align with the dietary preferences of the user.

Particular embodiments may comprise one or more of the following features. The plurality of foods comprises specific menu items from at least one restaurant. The plurality of foods comprises recipe ingredients of a home-cooked meal. The information about nutritional needs comprises genetic modifiers information about how different genes, genotypes, and genomes react to each micronutrient and combination of micronutrients. The genetic information of the user comprises at least one of a gene, a genome, a genotype, and a single nucleotide polymorphism (SNP) of the user. Outputting a warning for the user not to eat particular foods of the plurality of foods based on at least one of the genetic information, the medical information, and the therapeutic objectives of the user.

Aspects of this disclosure relate to a genetically personalized food recommendation system comprising: a processor communicatively coupled to a network and configured to receive at least two of genetic information, medical information, therapeutic objectives, and dietary preferences from each of a plurality of users through the network; and a storage communicatively coupled to the processor, the storage comprising a user library and a food micronutrient database, wherein the user library comprises a plurality of user profiles corresponding to the plurality of users, each of the user profiles comprising at least two of the genetic information, the medical information, the therapeutic objectives, and the dietary preferences of one of the plurality of users, wherein the food micronutrient database comprises food nutrient data for a plurality of foods and a mapping of individual micronutrients to at least two of genetic information, medical information, and therapeutic objectives, and wherein the processor is configured to: receive a food recommendation request from one of the plurality of users through the network; retrieve information regarding the genetic information, the medical information, the therapeutic objectives, and the dietary preferences of the one of the plurality of users from the user library and data from the food micronutrient database; identify one or more micronutrients that match any of the genetic information, the medical information, and the therapeutic objectives of the one of the plurality of users based on the mapping; identify at least one of the plurality of foods that provides the one or more micronutrients and aligns with the dietary preferences of the one of the plurality of users; and send a food recommendation comprising the at least one of the plurality of foods to the one of the plurality of users through the network.

Particular embodiments may comprise one or more of the following features. The plurality of foods comprises specific menu items of at least one restaurant. The plurality of foods comprises recipe ingredients of a home-cooked meal. The genetic information of the one of the plurality of users comprises at least one of a gene, a genome, a genotype, and a single nucleotide polymorphism (SNP) of the user. The processor is further configured to output a warning for the one of the plurality of users not to eat particular foods of the plurality of foods based on at least one of the genetic information, the medical information, and the therapeutic objectives of the one of the plurality of users. The processor is further configured to receive input from each of the plurality of users indicating foods of the plurality of foods that each of the plurality of users have consumed.

The foregoing and other aspects, features, applications, and advantages will be apparent to those of ordinary skill in the art from the specification, drawings, and the claims. Unless specifically noted, it is intended that the words and phrases in the specification and the claims be given their plain, ordinary, and accustomed meaning to those of ordinary skill in the applicable arts. The inventors are fully aware that he can be his own lexicographer if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those of ordinary skill in the art from the specification, drawings, and the claims.

BRIEF DESCRIPTION OF THE DRAWINGS

The disclosure will hereinafter be described in conjunction with the appended drawings.

FIG. 3 shows a representative initial mapping of micronutrients to genetic information, symptoms, conditions, and therapeutic objectives according to some embodiments.

DETAILED DESCRIPTION

Figure 1:
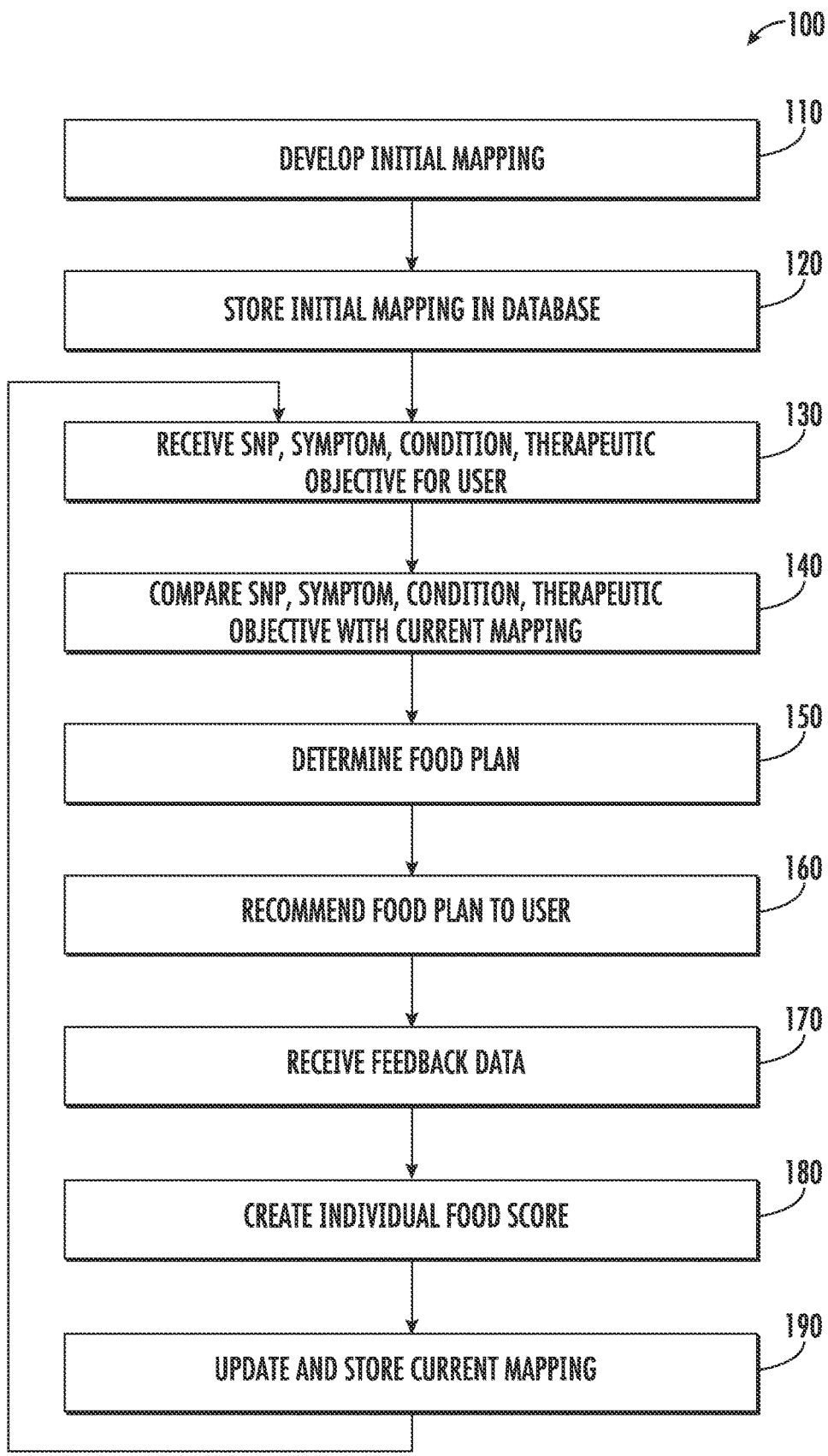
FIG. 1 shows a process flow for providing genetically personalized food recommendations according to some embodiments.

This disclosure, its aspects and implementations, are not limited to the specific components, methods, or other examples disclosed herein. Many additional components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented but have been omitted for purposes of brevity.

While this disclosure includes a number of implementations in many different forms, the drawings show particular implementations that will be described in detail with the understanding that the present disclosure is to be considered as an exemplification of the principles of the disclosed methods and systems and is not intended to limit the broad aspect of the disclosed concepts to the implementations illustrated.

Achieving and maintaining optimal health and proper function of the human body requires proper nutrition, including a correct balance of nutrients such as macronutrients (e.g., proteins, carbs, fats) and micronutrients (e.g., vitamins, minerals, electrolytes, antioxidants). Food micronutrient databases have been created to aid individuals in understanding the nutrients found in different foods and making decisions about which foods to consume. Different micronutrient databases may suggest different amounts of food for consumption based on the type of food and the nutrients found therein. However, current food micronutrient databases make assumptions about the optimal amounts of nutrients to consume based on broad averages, without looking at the individual's specific needs. Because each individual is unique and has different requirements for nutrients, the recommendations for the general public may not actually correlate to what any specific individual needs. Thus, current food micronutrient databases may suggest foods and amounts of food that could result in excess unnecessary nutrients or omit vital ingredients, compromising the ability of the food micronutrient database to provide recommendations that accurately portray the needs of the individual.

The present disclosure describes systems and methods that provide genetically personalized food recommendations. It has been found that individuals with different genotypes or genomes may need more or less of different nutrients. For example, due to differences in genetic makeup, a first individual may be able to consume any amount of carbs without it negatively affecting their health, while a second individual may need to avoid more than a small amount of carbs to avoid unwanted weight gain. The system disclosed herein is personalized for each individual based on their genetic makeup and is designed to recommend food that will meet each individual's nutritional needs. As will be described in more detail below, these individual needs may be determined based on genetic data and test results, among other things. Thus, each individual can receive food recommendations that can lead to the correct balance and amount of nutrients, including macronutrients (e.g., proteins, carbs, fats) and micronutrients (e.g., vitamins, minerals, electrolytes, antioxidants). Some implementations may focus on only some of these nutrients and may include nutrients not listed as well. Each element of the implementations discussed below may be implemented alone, or in conjunction with each of the other described elements.

In some embodiments, the food recommendations are also or alternatively personalized based on other medical data. Thus, an individual's nutritional needs may also be determined based on medical history and/or medical data and test results, among other things.

In some embodiments, the systems and methods disclosed herein facilitate determining which nutrients are needed for certain combinations of genetic information and medical information. For example, micronutrients may be matched to certain genetic information (e.g., a gene, a single nucleotide polymorphism ("SNP"), a genotype, etc.), symptoms, conditions, therapeutic objectives, and/or combinations of these attributes based on existing scientific literature. The matching of micronutrients to genetic information, symptoms, conditions, and/or therapeutic objectives may be repeatedly updated based on outcomes of the food recommendations, which may facilitate food recommendations to become more and more personalized to an individual's specific situation.

Updating micronutrient matches is not limited to being based on a single individual's past food recommendations, nor is it limited for application to a single individual's future food recommendations. Rather, the methods and systems allow for updating micronutrient matches for any individuals that will receive food recommendations in the future as soon as an outcome of a food recommendation is received by the system, even if these individuals are positioned geographically remotely from each other (i.e., they are acting on food recommendations in different parts of the world (e.g., different neighborhood, city, county, state, country, etc.)). Thus, the systems and methods may recommend food and micronutrients that most closely match individual needs based on all available individual medical information, genetic information, and therapeutic objectives, and most current aggregated feedback based on real individuals with similar genes and symptoms. In some embodiments, the methods and systems create a feedback loop of automatically applying food recommendation feedback data so that all new food recommendations include the feedback data received from all previous individuals who received food recommendations through the system.

The food recommendation system may also sequentially improve recommendations based on user preference to promote sustainability. For example, if the user's micronutrient profile (e.g., the micronutrients matched to the user's genetic information, medical information, and/or therapeutic objectives) suggests certain foods are unhealthy, the food recommendation system would be able to make recipe recommendations based on individual taste and outcome goals or provide feedback when a food product is scanned. Using weight loss as another example, general nutritional doctrine suggests that carbohydrate consumption causes weight gain, but this doesn't apply to all individuals. Thus, the food recommendation system may provide the proper food recommendation for weight loss based on genetic predispositions and help the user eat what they like (e.g., through the user's dietary preferences and/or from user feedback as the user acts on food recommendations), as opposed to placing the user on a generalized restrictive and non-sustainable diet. This empowers the user to take control of their own health and achieve the best outcome.

Users of the personalized food recommendations disclosed herein may experience improved disease prevention and treatment, prevention of aging, maintenance of metabolic function, and improved growth and development as a result of the personalized food recommendations.

In some embodiments, food recommendations may be personalized by collecting medical and genetic data regarding the user (including therapeutic objectives) as well as the user's dietary preferences, analyzing the medical and genetic data to determine the nutritional needs of the user (e.g., based on a nutritional formulary mapping nutrients to various medical and genetic data), selecting one or more foods from a plurality of foods stored in a food micronutrient database that provide the nutritional needs of the user, recommending the selected foods that also align with the user's dietary preferences, receiving input from the user on the food that the user consumed, collecting feedback from the user regarding the effect of the consumed food, and adjusting the nutritional formulary to incorporate the feedback provided. The feedback may be objective and/or subjective. In addition, the feedback may relate to dietary preferences (e.g., whether the user enjoyed the consumed food) or it may relate to whether a medical condition improved or whether progress was made on reaching a therapeutic objective.

Any medical and genetic data can be relevant. Therefore, to provide the personalized food recommendations disclosed herein, the data collected may include, but is not limited to, blood test results, genetic test results, vital signs (e.g., blood pressure, heart rate, heart rhythm, etc.), biometric data, data received from wearable devices, lifestyle data (such as travel and recent infections or vaccinations), medical histories, medical diagnoses, diseases of which the recipient is at heightened risk, and current symptom descriptions. In addition, the data may include specific therapeutic objectives of the recipient, such as health goals, aesthetic goals, fitness goals, weight loss, increased energy, healthier skin or hair, or improved mental acuity (or others discussed below). As more data is included, the personalized food recommendations can be adapted to be more comprehensive and accurate in providing the nutritional needs for the user, and those same findings can be applied to improve personalized food recommendations for other users with similar conditions as well.

The medical and genetic data may be provided directly by the recipient or may be determined using medical and lab procedures. In some embodiments, some of the medical and genetic data is provided directly by the recipient and some of the medical and genetic data is determined using medical and lab procedures. For example, the recipient may provide a family medical history and a description of current symptoms, such as fatigue or headaches, while medical tests and procedures may be used to perform blood tests and genetic tests, as well as provide a medical diagnosis.

In some embodiments, the collected data may be mapped into a code to facilitate the interpretation of the data and enable its use in algorithms and automated systems. For example, an international classification system may be used, such as the International Statistical Classification of Diseases and Related Health Problems (ICD) implemented by the World Health Organization (WHO). The most current ICD code is the ICD-11. Any system of classification of diseases, symptoms, and genes may be implemented.

The collected data may be analyzed to determine the nutritional needs of the recipient. In some implementations of the personalized food recommendations disclosed herein, the collected data is analyzed by a life science professional who is familiar with the genes, diseases, and symptoms communicated by the data and understands what nutritional needs this data expresses. For example, experts in fields such as nutraceuticals, pharmacokinetics, pharmaceuticals, nutrition, nutritional science, nutrigenomics, biomedical sciences, food data sciences, and statistics may work together to review the collected data and determine which nutrients can help improve the health of the recipient.

In other implementations, this analysis may be automated. For example, a nutritional formulary or a mapping may be created which links each gene, disease, symptom, and therapeutic objective with different nutritional needs (e.g., micronutrients). Additionally, the nutritional formulary may indicate nutritional needs for specific combinations of symptoms, diseases, genes, and therapeutic objectives. For example, a first recipient may have a first symptom and a first gene. The nutritional formulary may suggest a first micronutrient to provide what the first recipient needs. A second recipient may have the same first symptom, but a second gene. In some cases, the nutritional formulary may suggest the same first micronutrient in the same amount. However, in other cases, the specific combination of the first symptom with the second gene may necessitate suggesting a second micronutrient or a different amount of the first micronutrient. Thus, the nutritional formulary is configured to take into account all of the collected data in determining the nutritional needs of the recipient. The nutritional formulary may be stored in a nutritional database. All references herein to a nutritional formulary may be considered a reference to a nutritional database. Likewise, all references to a nutritional database may be considered a reference to a nutritional formulary. The nutritional formulary or nutritional database may also be referred to as a mapping (i.e., mapping micronutrients to genetic information, symptoms, conditions, therapeutic objectives, and combinations of these attributes). The nutritional formulary may be used by an automated process or may be used by the experts discussed above.

The nutritional formulary, database, or mapping may be part of a food micronutrient database, which may also store food nutrient data for a plurality of foods. The food nutrient data may indicate the nutrients (e.g., macronutrients, micronutrients, etc.) provided by consuming a particular food. Thus, once the nutritional needs of the recipient have been determined, the genetically personalized food recommendation system may be designed to match individual micronutrient requirements to commercially available food products. The food micronutrient database may be used in a variety of situations. For example, the commercially available food products may be menu items from a restaurant or items for sale in a grocery store. The plurality of foods for which food nutrient data is stored in the food micronutrient database may also include recipe ingredients of a home-cooked meal. Some embodiments may be tailored to particular situations. For example, some embodiments may be tailored to recommending menu items at a restaurant. As another example, some embodiments may be tailored to providing advice and recommendations relating to a product at a grocery store. As yet another example, some embodiments may be tailored to providing recipe recommendations for making a home-cooked meal. Some embodiments may be configured for all these situations (and others). In some embodiments, in addition to food recommendations, the system may provide food warnings of foods not to eat.

In some embodiments, the user may indicate foods that have actually been consumed. For example, a user may indicate whether the user acted on the food recommendation. In addition, feedback may be collected from the user regarding the user's experience after consuming the food. For example, the user may provide feedback about any change (improvements or declines) in symptoms, vital signs, overall health and fitness, or physical or mental energy. The user may also provide feedback about progress towards reaching therapeutic objectives. Other types of feedback may also be received. For example, feedback may originate from measured bloodwork, epigenetic changes, or other sources. This feedback can then be used as a helpful datapoint in determining the effectiveness of the food recommendation/consumed food and whether each of the food items had the desired effect. In some embodiments, with multiple datapoints collected from various recipients, the nutritional database can be updated and improved. In some embodiments, the feedback may relate to the user's dietary preferences and whether the user enjoyed the consumed food.

In some embodiments, the food recommendations may be modified based on the feedback. For example, a first recipient with a particular gene may find success in achieving a particular health goal through consuming food with a first micronutrient, while a second recipient with the same health goal but a different gene may not be successful on the first micronutrient. Over time, with enough datapoints from recipients with the same therapeutic objective, it may be discovered that a particular gene interferes with the effectiveness of the first micronutrient, but that a second micronutrient can have the same effect. Once the nutritional database is updated to reflect this finding, the personalized food recommendations become more effective. For this reason, the feedback loop may provide an important benefit.

In a particular implementation, the recipient's genetic micronutrient requirement profile may be generated to illustrate the specific nutrients needed. This micronutrient requirement profile may be generated based on the collected data. Based on the recipient's micronutrient requirement profile, the food recommendations can be personalized to provide the recipient with vital ingredients in the amounts necessary. Moving forward, the food recommendations can be sequentially refined based on the recipient's goals combined with diagnostics to reach the desired outcomes of proper nutrition and optimal health.

An example method 100 of providing genetically personalized food recommendations is shown, for example, in FIG. 1. Although method 100 as shown in FIG. 1 includes a number of operations in a particular order, method 100 may include more or fewer operations and the operations may be completed in different orders. In addition or alternatively, in some embodiments, variations of the operations shown in FIG. 1 may be used as part of method 100.

In some embodiments, method 100 includes developing an initial mapping of genetic and/or medical data to micronutrients based on existing scientific literature at operation 110, storing the initial mapping in a database at operation 120, receiving genetic data (e.g., a single nucleotide polymorphism (SNP), a genome, gene, multiple SNPs, etc.) and/or medical data (e.g., symptoms, conditions, therapeutic objectives, vital signs, etc.) of a user at operation 130, comparing the genetic and medical data with the current mapping (e.g., the initial mapping or an updated mapping based on feedback from previous food recommendations and/or new scientific literature) at operation 140, determining a food plan or recommendation based on the comparison at operation 150, recommending the food plan to the user at operation 160, receiving feedback data based on the food recommendations and/or the consumed food at operation 170, creating an individual food score for the consumed food based on the feedback at operation 180, and updating and storing the current mapping based on the individual food score at operation 190. The method 100 may include repeating operations 130, 140, 150, 160, 170, 180, and 190 for multiple users that are geographically remote from each other.

Thus, in some embodiments, because feedback from food recommendations is constantly being used to update the mapping, the mapping will be more up to date than existing published science alone. In some embodiments, new scientific literature may be inputted to update the mapping, in addition to the feedback from food recommendations. Inputting both scientific literature and feedback from food recommendations helps keep the mapping as up to date as possible and contributes to greater accuracy and more personalization in the mapping.

In some embodiments, at operation 110, the initial mapping of genetic and/or medical data to micronutrients is developed. The mapping identifies the micronutrients that are suitable for users having particular genetics, particular symptoms, particular conditions, or particular therapeutic objectives based on the existing scientific literature. As discussed further below, the micronutrients may be mapped to various combinations of genetics, symptoms, conditions, and therapeutic objectives. For example, the micronutrients may be mapped to particular genetics, a particular symptom, a particular condition, and a particular therapeutic objective. The genetic data may be an SNP, a genome, a gene, multiple SNPs, or some other genetic data. The discussion below primarily refers to an SNP, but the same principles apply to using other types of genetic data and the disclosure includes other types of genetic data.

Figure 2:
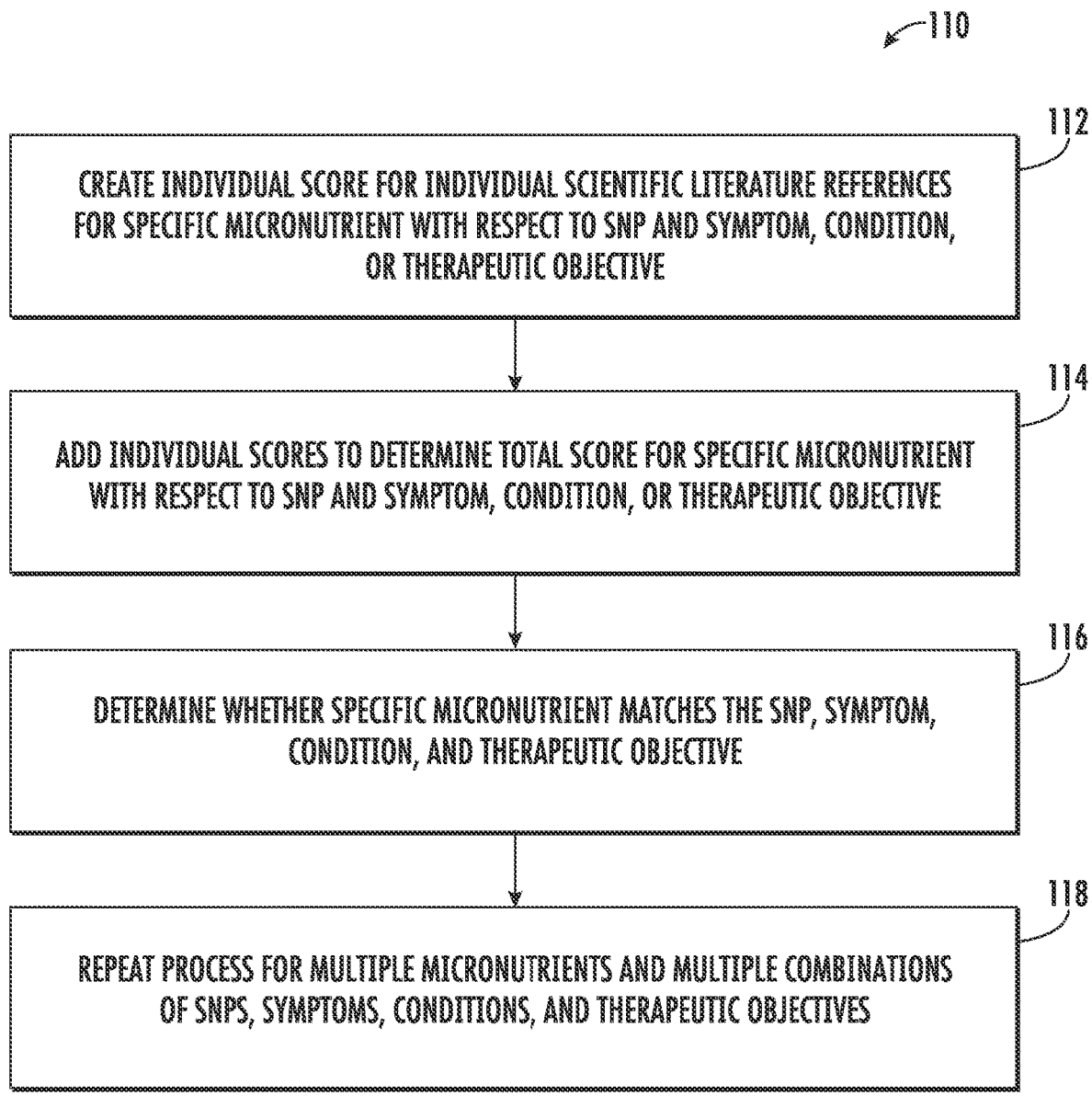
FIG. 2 shows a process flow for developing an initial mapping of micronutrients to genetic information, symptoms, conditions, and therapeutic objectives according to some embodiments.

An example process for operation 110 of developing an initial mapping is shown in FIG. 2. In some embodiments, at operation 112, an individual score is created for individual scientific literature references for a specific micronutrient with respect to an SNP (or some other type of genetic data) and a symptom, condition, or therapeutic objective (or a combination of a symptom, condition, and/or therapeutic objective). An individual score may be created for every available scientific literature reference. A reference may have multiple individual scores if the reference discusses multiple micronutrients, multiple SNPs, multiple symptoms, multiple conditions, or multiple therapeutic objectives. For example, the reference may receive an individual score for each unique combination of micronutrient, SNP, symptom, condition, and/or therapeutic objective discussed in the reference.

An individual score may be positive or negative. A positive score is created when the individual scientific literature reference provides evidence of a positive connection between a micronutrient and an SNP, symptom, condition, therapeutic objective, or a combination of two or more of these characteristics. A negative score is created when the individual scientific literature reference provides evidence of a negative connection between a micronutrient and an SNP, symptom, condition, therapeutic objective, or a combination of two or more of these characteristics. In some embodiments, a scientific literature reference that provides a non-statistically significant outcome may also receive a negative score.

In some embodiments, the individual score may be zero. For example, in some embodiments, a score of zero may be created for references that provide a non-statistically significant outcome. In some embodiments, only studies that have a statistical significance assessment are scored. For example, case series and reports may be logged but do not affect the scoring, due to a low level of scientific evidence. On the other hand, randomized controlled trials, meta-analyses, and observational studies may be scored.

In some embodiments, the individual score may be weighted based on various factors. For example, the individual score may be weighted based on the strength of the findings in the reference, the number of categories (e.g., SNP, symptom, condition, therapeutic objective) analyzed in the reference, or the category that had a connection (e.g., a connection for an SNP may be weighted higher than a connection for a therapeutic objective, etc.). Other factors may also be used. As one example, in some embodiments, a reference that relates to an outcome of consuming food having a micronutrient may be given an individual score that has more weight than an individual score of a reference that relates to an injectable outcome or an oral supplements outcome.

In some embodiments, at operation 114, individual scores relating to a specific micronutrient may be added together to determine a total score for the specific micronutrient with respect to an SNP (or some other type of genetic data) and a symptom, condition, or therapeutic objective (or a combination of a symptom, condition, and/or therapeutic objective). In some embodiments, at operation 116, it is determined whether the specific micronutrient matches the SNP, symptom, condition, and therapeutic objective. For example, if the total score for the micronutrient with respect to the SNP, symptom, condition, and therapeutic objective exceeds a predetermined threshold, then the micronutrient is determined to match the SNP, symptom, condition, and therapeutic objective. This may be repeated for each combination of SNP, symptom, condition, and therapeutic objective so that the method identifies all the scenarios for which the specific micronutrient is a good match.

In some embodiments, at operation 118, this scoring process (i.e., operations 112, 114, and 116) is repeated for multiple micro-nutrients and multiple combinations of SNPs, symptoms, conditions, and therapeutic objectives to develop the initial mapping. A schematic representing an example initial mapping 200 is shown in FIG. 3. For simplicity, FIG. 3 only shows two micronutrients ($M_1$ and $M_2$), two SNPs ($SNP_1$ and $SNP_2$), two symptoms ($S_1$ and $S_2$), two conditions ($C_1$ and $C_2$), and two therapeutic objectives ($TO_1$ and $TO_2$). However, initial mapping 200 may include many more micronutrients, SNPs, symptoms, conditions, and/or therapeutic objectives.

The schematic of initial mapping 200 includes mapping columns 210 that include series of cells 260 that indicate whether the micronutrient matches the combination of SNP, symptom, condition, and therapeutic objective in that particular row. A checkmark indicates a match. To the left of mapping columns 210 are an SNP column 220, a symptom column 230, a condition column 240, and a therapeutic objective column 250. In some embodiments, changing the SNP, symptom, condition, or therapeutic objective (and keeping the other factors the same) may result in a different recommended micronutrient. In some embodiments, multiple micronutrients may be matched with the same combination of SNP, symptom, condition, and therapeutic objective.

In some embodiments, the initial mapping 200 provides a specific amount of a micronutrient for a specific combination of SNP, symptom, condition, and therapeutic objective, in addition to identifying which micronutrient is a match. In particular, when scientific literature provides evidence of the right amount of a micronutrient to use for a particular SNP, symptom, condition, and/or therapeutic objective, this detail may be included in the mapping. In some embodiments, scientific literature providing evidence of an amount may be scored to determine the recommended amount. In some embodiments, the amount evidence is not scored, but is simply used as a guideline (until further information becomes available through food recommendations and feedback about the results).

In some embodiments, there may be holes in the initial mapping 200. For example, there may not be sufficient scientific literature for a certain micronutrient, SNP, symptom, condition, or therapeutic objective to determine whether there is a good match. In some embodiments, the method may include making a best guess based on similar or related micronutrients, SNPs, symptoms, conditions, or therapeutic objectives. As discussed below, method 100 refines the results continuously over time. In some embodiments, the initial mapping may begin less specific (e.g., the recommended micronutrient is the same for a given symptom, condition, and therapeutic objective regardless of genetic information) with the mapping becoming more specific as process 100 is used (e.g., the recommended micronutrient for a given symptom, condition, and therapeutic objective differs depending on genetic information). The increased specificity is not limited to genetic information, but may also be based on symptoms, conditions, and/or therapeutic objectives. For example, the initial mapping may map a micronutrient to a given SNP, symptom, and condition, regardless of the therapeutic objective, while the mapping may be updated through process 100 so that the recommended micronutrient for the given SNP, symptom, and condition differs depending on the therapeutic objective.

In some embodiments, the mapping relates solely to genetic information (e.g., SNPs) and suitable micronutrients (potentially including amount and frequency). Feedback through food recommendations may likewise focus solely on genetic information rather than considering medical information in addition to genetic information. In some embodiments, the mapping relates solely to clinical presentations (e.g., symptoms or conditions) and suitable micronutrients (potentially including amount and frequency). In some embodiments, any combination of genetic information, medical information, symptoms, conditions, and therapeutic objectives (including each one individually) may be mapped to suitable micronutrients (potentially including amount and frequency). This same principle applies to other implementations disclosed herein. Specifically, the methods and systems disclosed herein may focus only on SNPs in identifying suitable micronutrients, only on clinical presentations, only on symptoms, only on conditions, only on therapeutic objectives, or any combination of these factors.

In addition, while the method of FIG. 1 focuses on food recommendations (and micronutrients provided by foods), in some embodiments, the mapping may be to oral supplement nutrients, and in particular to oral supplement micronutrients, or to intravenous or intramuscular nutrition therapy. This same principle applies to other implementations disclosed herein. Specifically, the methods and systems disclosed herein may relate to oral supplement treatments or intravenous/intramuscular nutrition therapy, instead of food recommendations. In the context of oral supplements treatments, again, the mapping may be of clinical presentations to oral supplement micronutrients, SNPs to oral supplement micronutrients, or a combination of clinical presentation and SNPs to oral supplement micronutrients. The same is true for intravenous/intramuscular nutrition therapy.

Returning to FIG. 1, in some embodiments, at operation 120, the initial mapping 200 is stored in a database. In some embodiments, the individual scores of the scientific literature references for each micronutrient, SNP, symptom, condition, and therapeutic objective combination are also stored in the database. The added scores (or the total scores) for each micronutrient, SNP, symptom, condition, and therapeutic objective combination may also be stored in the database. The database may be part of a server and made available over a network to electronic devices, as discussed in more detail below with respect to FIG. 8. The electronic devices accessing the database over the network may be user electronic devices, such as a smartphone, tablet, or personal computer. Because the initial mapping 200 is stored in a database available over a network, the mapping can be updated in real time by food recommendations that occur in different geographic locations through the remaining operations of method 100. Although the remaining operations of method 100 are described for a single user, these operations may be repeated many times for multiple users to update the mapping and improve the accuracy of the mapping.

In some embodiments, at operation 130, an SNP, symptom, condition, or therapeutic objective are received for a user. In some embodiments, all four of an SNP, symptom, condition, and therapeutic objective are received. In some embodiments, only a subset of an SNP, symptom, condition, and therapeutic objective are received. For example, an SNP for a user and at least one of a symptom, a condition, and a therapeutic objective of a user may be received (e.g., SNP and symptom; SNP and condition; SNP and therapeutic objective; SNP, symptom, and condition; etc.). Multiple SNPs, symptoms, conditions, and therapeutic objectives may be received for the user. For example, if the user has multiple symptoms, each symptom may be included. This information may be entered into fields on an electronic device by the user. In some embodiments, a user may have a profile that stores information from previous food recommendations. When a user uses the system for another food recommendation, the system may automatically retrieve the stored information (e.g., regarding SNPs, symptoms, conditions, therapeutic objectives). Because symptoms, conditions, and therapeutic objectives may change over time, the user may either confirm or edit this information.

In some embodiments, the SNP, symptom, condition, or therapeutic objective may be determined by a test kit or monitoring equipment. For example, a genetic testing kit may be used to determine the user's genetic information, including an SNP. Additional examples of monitoring equipment that may determine symptoms or conditions (or contribute to determining a therapeutic objective) include thermometers, scales, blood pressure monitors, blood glucose monitors, heart rate monitors, pulse oximeters, electrocardiographs, etc.

After receiving the user's SNP, symptom, condition, and therapeutic objective (or a subset, such as an SNP and at least one of a symptom, condition, and therapeutic objective), this information may be compared with the current mapping stored in the database at operation 140. For the first user, the current mapping may be the initial mapping 200. Once feedback from a food recommendation has been received, the current mapping may be an updated mapping based on that feedback. Comparing the user's information with the current mapping identifies one or more micronutrients that have been matched to the SNP, symptom, condition, and therapeutic objective (or a subset, such as an SNP and at least one of a symptom, condition, and therapeutic objective).

In some embodiments, at operation 150, a food plan may be determined for the user based on the one or more micronutrients identified from the current mapping (e.g., initial mapping 200 or an updated mapping). The food plan comprises one or more foods that provide the identified micronutrients. The food plan may be determined with reference to a food micronutrient database that stores food nutrient data for a plurality of foods. In some embodiments, the food plan is a short-term food plan. For example, the food plan may relate to what a user should eat right now or at the next meal. A short-term food plan may be determined in response to a user requesting a food recommendation (e.g., when wanting a snack, at mealtime, etc.). A short-term food plan may be used in a variety of contexts, including, for example, at a restaurant when deciding what to eat from the menu, at a grocery store when deciding what to purchase, and at home when deciding what to prepare. In some embodiments, the food plan is a long-term food plan. For example, the food plan may provide recommendations for an extended period of time (e.g., one day, several days, one week, several weeks, one month, several months, etc.) that will help a user consume the right micronutrients and the right amount of each micronutrient based on the user's genetic information, medical information, and/or therapeutic objectives.

In some embodiments, the food plan may also account for dietary preferences of the user. A user may input dietary preferences (including allergy information, lifestyle information, likes/dislikes, etc.) into the system. For example, if a user is vegetarian, the system will not recommend a food plan that contains meat. Dietary preferences may be tailored to certain situations. For example, a user may prefer to not eat certain foods too early or too late in the day. As another example, a user's dietary preferences may depend on the food that the user has recently consumed.

At operation 160, the food plan determined at operation 150 is recommended to the user. In some embodiments, at operation 170, feedback data relating to the food recommendation is received. As part of the feedback data, the user may indicate which food the user actually consumed (whether it was in line with the recommendation, a variation of what was recommended, or some other food). The feedback data may be about an effectiveness of the food recommendation (or the consumed food if different than the recommendation) in addressing a symptom, a condition, or a therapeutic objective of the user (or a combination of a symptom, condition, and therapeutic objective).

In some embodiments, the feedback data may include objective feedback (e.g., test results) and/or subjective feedback (e.g., survey responses). For example, the feedback data may include feedback about measured bloodwork (e.g., comparing bloodwork from before and after the food recommendation), epigenetic changes, improvements or declines in symptoms, progress towards reaching therapeutic objectives, vital signs, overall health and fitness, or physical or mental energy. Other types of feedback may also be used. For example, the feedback data may relate to dietary preferences. If a user did not like the food that was recommended, the user can input this feedback, so the system does not recommend the food again. Alternatively, if the user really liked the food that was recommended, the user can input this feedback, so the system will continue to recommend the food (when appropriate based on the genetic information, medical information, and therapeutic objectives).

In some embodiments, at operation 180, an individual food score is created based on the feedback data. In some embodiments, the individual food score does not consider any feedback relating to dietary preferences. The individual food score may be for the identified one or more micronutrients in the food recommendation with respect to the user's SNP and symptom, condition, and therapeutic objective (or a subset). Similar to the scores for scientific literature, individual food scores may be positive or negative. For example, when the food recommendation (or any consumed food) results in improvement in the symptom, a positive individual food score may be created for the micronutrients contained in that food. On the other hand, if the symptom worsens, a negative score may be created. The individual food score may be based on a single factor (e.g., whether the symptom improved or declined), or the score may be based on multiple factors (e.g. change in symptom(s), progress for reaching therapeutic objective, vital signs, energy levels, etc.).

In addition, individual food scores may be weighted depending on the feedback data. For example, the individual food score may be commensurate with how much a symptom improves or declines and/or how much progress is made (or lost) towards reaching a therapeutic objective. Thus, the more the symptom improves, the higher the individual food score will be. As another example, the more progress is made towards the therapeutic objective, the higher the individual food score will be.

In some embodiments, multiple individual food scores may be created for a single food recommendation or consumed food. For example, if a symptom declines but progress is made toward a therapeutic objective, a negative score may be made for the combination of the SNP, symptom, and therapeutic objective while a positive score may be made for the combination of the SNP and therapeutic objective without that symptom.

In some embodiments, individual food scores may be weighted based on multiple factors. Certain factors may have greater weight than others. For example, whether the symptom improves may have greater weight than measured bloodwork or vice versa.

Figure 4:
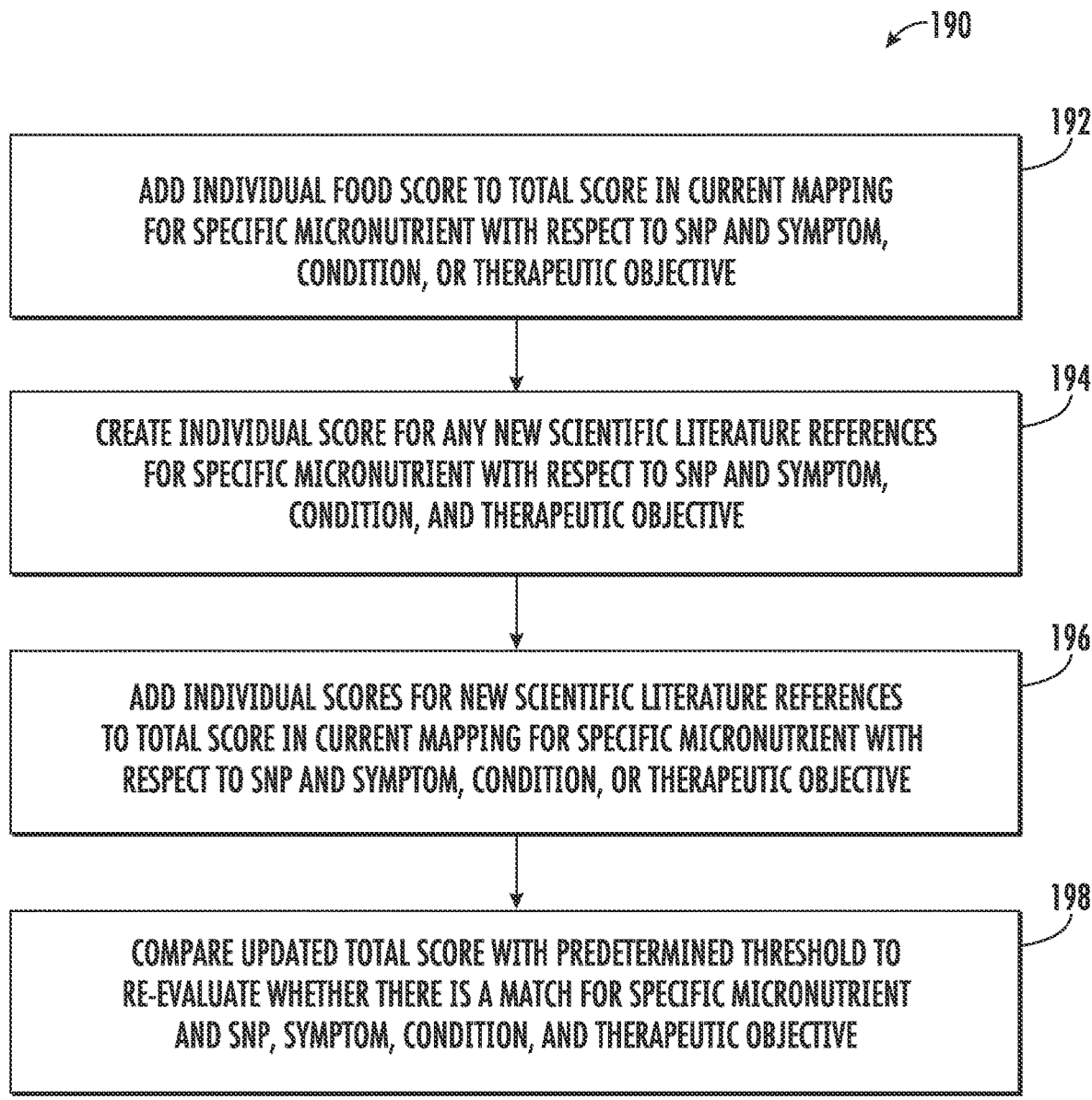
FIG. 4 shows a process flow for updating a mapping of micronutrients to genetic information, symptoms, conditions, and therapeutic objectives according to some embodiments.

In some embodiments, at operation 190, the current mapping is updated and then stored in the database. As noted above, for the first user, the current mapping may be the initial mapping 200. Once feedback from food recommendations has been received, the current mapping may be an updated mapping based on that feedback. An example process for operation 190 of updating a current mapping is shown in FIG. 4.

In some embodiments, at operation 192, an individual food score (e.g., from a food recommendation for a first user) is added to a total score in the current mapping (e.g., initial mapping 200) for the specific micronutrient(s) used for the food recommendation with respect to the SNP and symptom, condition, and therapeutic objective (or a subset) of the user. To illustrate this principle, if a user has a GP×1 gene SNP, a headache as a symptom, fibromyalgia as a condition, and weight loss as a therapeutic objective, the individual food score may be tied to this combination of SNP, symptom, condition, and therapeutic objective. Thus, this individual food score would be added to the total score from the current mapping of the GP×1 gene SNP, headache symptom, fibromyalgia condition, and weight loss therapeutic objective.

In some embodiments, at operation 194, an individual score is created for any new scientific literature references that have not previously been taken into account (to the extent there are any). Thus, if a new study has linked a specific micronutrient to an SNP, symptom, condition, or therapeutic objective (or a combination of some or all of these), an individual score is created for each relevant combination of micronutrient, SNP, symptom, condition, and therapeutic objective. The principles discussed above for creating individual scores for scientific literature references equally apply to any new references.

In some embodiments, at operation 196, the individual scores for any new scientific literature references are added to the total score in the current mapping (in addition to the added individual food scores added in operation 192). The updated total score (based on the addition in operation 192 and/or operation 196) may be stored in the database.

In some embodiments, at operation 198, the updated total score is compared with a predetermined threshold (e.g., the same predetermined threshold used when evaluating the total score to develop the initial mapping 200). This comparison allows for reevaluating whether there is a match between a specific micronutrient and an SNP, symptom, condition, and therapeutic objective combination. This process of updating the current mapping ensures that the mapping is based on the latest scientific literature and real time results of actual food recommendations/consumed food. Similar comparisons may be made to determine appropriate amount, frequency, etc. of the micronutrients or food plan.

In some embodiments, fewer or more operations than are shown in FIG. 4 may be used to update a current mapping. For example, the mapping may be updated based only on food recommendations, only on new scientific literature references, or a combination of food recommendations and scientific literature references. The order of the operations may differ from what is shown in FIG. 4.

Additional examples of methods of providing personalized food recommendations will now be discussed with respect to FIGS. 5-7. Variations of these examples (and other examples discussed herein) may be used. For example, operations from one example may be combined with operations from another example. In addition, details discussed with respect to one example may equally apply to other examples. These example methods may be implemented with the system described below with respect to FIG. 8.

Figure 5:
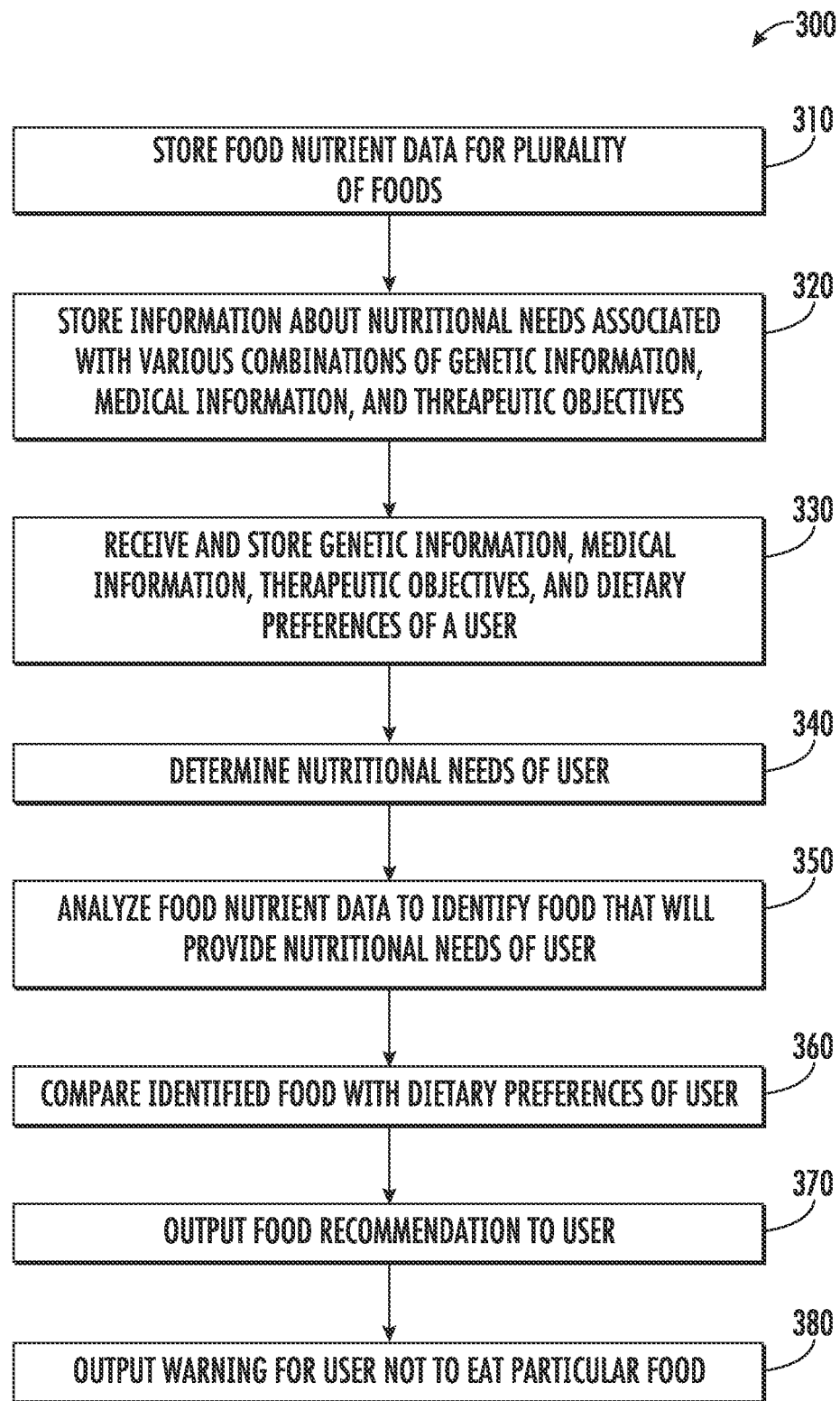
FIG. 5 shows a process flow for providing genetically personalized food recommendations according to some embodiments.

FIG. 5 illustrates a method 300 of providing genetically personalized food recommendations. In some embodiments, at operation 310, food nutrient data is stored for a plurality of foods. The food nutrient data may be stored in a food micronutrient database. For each food, the food nutrient data may include proximates data, inorganics data, micronutrients data, vitamin fractions data, fatty acid compositions data, and/or bioactive compounds data. Thus, a complete picture of the nutrients obtained by consuming a particular food is stored in the food micronutrient database. In some embodiments, the plurality of foods comprises menu items from a restaurant or from multiple restaurants. In some embodiments, the plurality of foods comprises any food product for sale at a grocery store. In some embodiments, the plurality of foods comprises home-cooked meals and/or recipe ingredients of a home-cooked meal. The plurality of foods may include any beverage. In short, any food or drink may be included in the plurality of foods.

Additional foods may be added to a database over time. For example, new restaurants may provide their menus and food nutrient data of the menu items to a database to be stored, restaurants may provide the food nutrient data of new menu items to a database to be stored, food and beverage producers may provide the food nutrient data of the items they produce to a database to be store, and/or users may add recipes to a database so that associated food nutrient data of the recipe ingredients may be stored. Thus, the stored data may be dynamic.

In some embodiments, at operation 320, information about nutritional needs associated with various combinations of genetic information, medical information, and therapeutic objectives may be stored. This information about nutritional needs may be stored in the food micronutrient database so that the same database links micronutrients to genetic information, medical information, and/or therapeutic objectives and links to particular foods to micronutrients. The information about nutritional needs may be the mapping of micronutrients to genetic information, medical information, symptoms, conditions, and/or therapeutic objectives discussed above. In some embodiments, the information about nutritional needs includes genetic modifiers information about how different genes, genotypes, and genomes react to each micronutrient and combination of micronutrients. As discussed above, this information about nutritional needs may be updated over time based on feedback from users of a food recommendation system and/or based on new scientific literature that links micronutrients to certain genetic information, medical information, and/or therapeutic objectives.

At operation 330, genetic information, medical information, therapeutic objectives, and/or dietary preferences of a user may be received. In some embodiments, this information is stored in a user library. For example, a user profile containing this information and other identifying information for that particular user may be created and stored in a user library. The user library may be coupled to or in communication with the food micronutrient database. In some embodiments, the user may provide this information by inputting information into an electronic device that is communicatively coupled with the user library and/or the food micronutrient database (e.g., via a network). In some embodiments, a third party may provide this information (e.g., a healthcare provider of the user).

In some embodiments, the genetic information of the user comprises genetic test results. The genetic information of the user may comprise a gene, genome, genotype, SNP, or other piece of genetic data. In some embodiments, the genetic information comprises epigenetic measurements (e.g., epigenetic clocks, methylation scores, etc.)

In some embodiments, the medical information may include blood test results, vital signs (e.g., blood pressure, heart rate, heart rhythm, etc.), medical histories, medical diagnoses, current symptoms, diseases of which the patient is at heightened risk, family history, or other medical information. Medical information may include biodata that is captured and measured through various processes, which may include blood testing, urine sampling (e.g., toxicology screens, etc.), stool sampling, continuous blood glucose monitoring, and imaging/scanning (e.g., ultrasound, etc.). Devices may include blood pressure monitors, heart rate monitors, body hydration monitors, breathalyzers, blood glucose monitors, metabolic devices, pulse oximeters, and wearable devices configured to measure any type of biodata.

A variety of therapeutic objectives may be used as inputs. For example, the therapeutic objectives may comprise health goals, aesthetic goals, or fitness goals. The therapeutic objectives may be to lose weight, to gain weight, to improve fitness level, to improve energy levels, to alter skin tone (to either a darker tone or a lighter tone), to improve skin quality and/or health, to improve hair quality and/or health, to improve mental acuity, to prevent disease, to improve symptoms of an existing illness or disease, to improve sleep quality, to improve longevity/anti-aging, to protect against excessive stress, to protect against toxin exposures (e.g., from pollution, chemicals, alcohol, etc.), to rehydrate, to support immune health, and/or to heal a wound. Other therapeutic objectives may also be used.

In some embodiments, at operation 340, nutritional needs of the user are determined. This determination may be based on the genetic information, the medical information, and/or the therapeutic objectives of the user and the information about nutritional needs stored in the food micronutrient database associated with the user's combination of genetic information, medical information, and therapeutic objectives. Other considerations may also be taken into account, such as foods that the user has recently consumed. In some embodiments, the nutritional needs may be immediate needs (e.g., what micronutrients does the user need for the next snack or meal) or they may be over a period of time, such as a day, week, month, or some other time period.

In some embodiments, at operation 350, the food nutrient data stored in the food micronutrient database is analyzed to identify food that will provide the nutritional needs of the user. The analysis may lead to identifying one food (e.g., a particular snack, a particular dish, a particular menu item, etc.) or multiple foods (e.g., multiple menu items, a main dish with one or more sides, etc.). The identified food may be for immediate consumption or spread over time (similar to the nutritional needs discussed in the previous paragraph). The identified food may include multiple options that would satisfy the nutritional needs (e.g., either a first menu item or a second menu item, etc.)

In some embodiments, at operation 360, the identified food is compared with dietary preferences of the user. For example, where there are multiple options that would satisfy the user's nutritional needs, this comparison may prioritize certain options (e.g., where a user has indicated a preference for a certain type of food). Alternatively, this comparison may rule out certain options (e.g., where a user is vegetarian, any meat-based option would be ruled out).

In some embodiments, at operation 370, a food recommendation is outputted to the user. The food recommendation may include food selected from the identified foods that also align with the dietary preferences of the user. The food recommendation may be for immediate consumption or spread over time (similar to the nutritional needs discussed above). For example, the food recommendation may be a food plan for an upcoming day or week. In some embodiments, the food recommendation is sent over a network to the user's electronic device.

In some embodiments, at operation 380, a warning for the user not to eat particular food may be outputted. For example, where a food will be particularly harmful to a user's health based on the genetic information, the medical information, and/or the therapeutic objectives of the user, the user may receive a warning (e.g., at an electronic device) not to eat that food.

In some embodiments, fewer or more operations than are shown in FIG. 5 may be used to provide personalized food recommendations. For example, operation 380 and/or operation 360 may be omitted. As another example, an operation associated with receiving feedback may be included (as discussed above). The order of the operations may differ from what is shown in FIG. 5.

Figure 6:
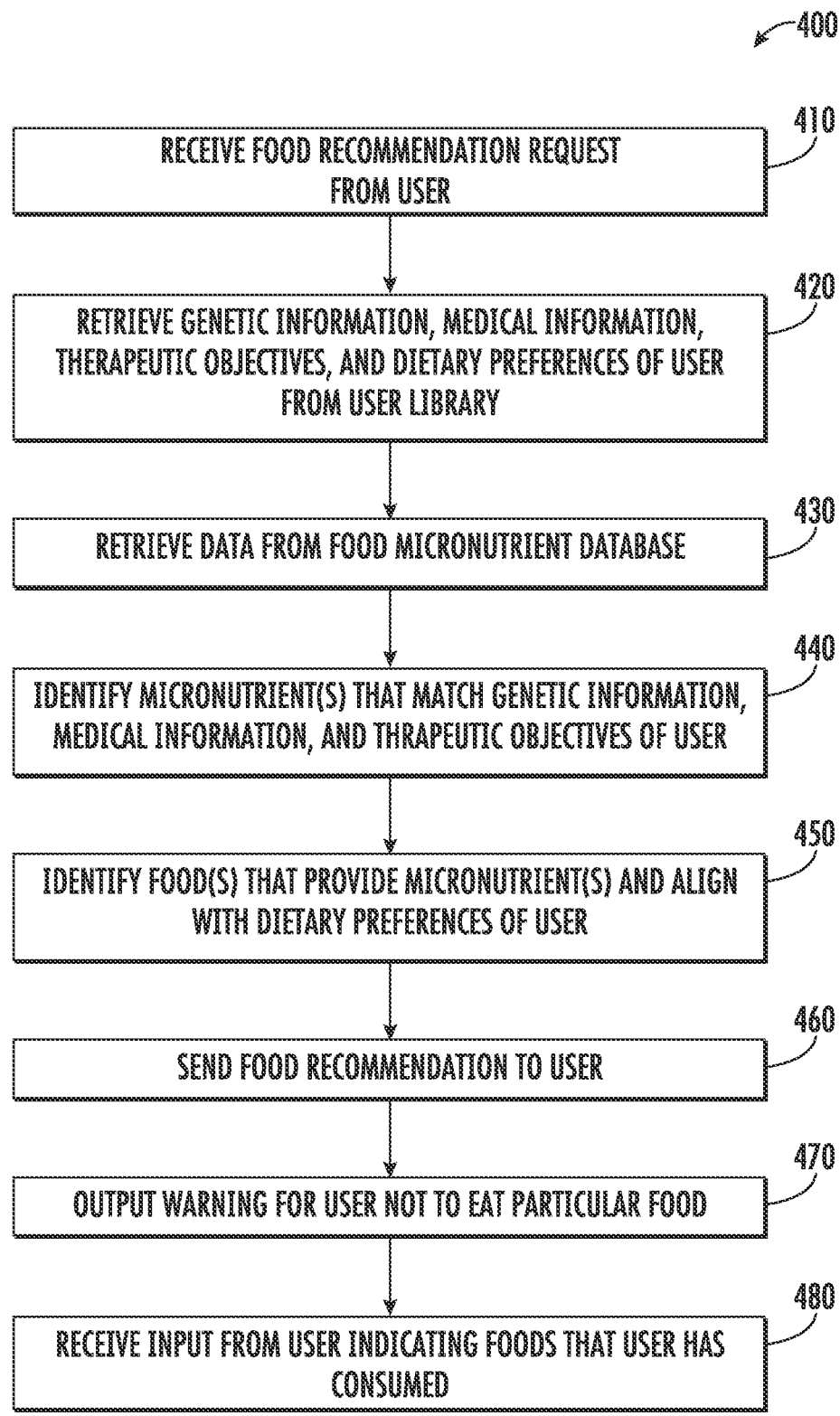
FIG. 6 shows a process flow for providing genetically personalized food recommendations according to some embodiments.

FIG. 6 illustrates a method 400 of providing genetically personalized food recommendations in response to user requests. In some embodiments, at operation 410, a food recommendation request from a user is received. The food recommendation request may be for general recommendations (e.g., what types of food are healthy for the user to consume). Alternatively, the food recommendation request may include a specific food which the user desires to eat and ask for information regarding the health implications of consuming that food. In some embodiments, the specific food may be scanned (e.g., by a user's electronic device in a grocery store or off a restaurant's menu) to produce the request. The food recommendation request may also indicate that the user is at a specific restaurant and ask which dish on the menu or on a narrowed list of menu items is best. The food recommendation request may ask for any information regarding food and food choices.

In some embodiments, at operation 420, genetic information, medical information, therapeutic objectives, and/or dietary preferences of the user are retrieved from a user library. The user library may include a plurality of user profiles corresponding to a plurality of users, each of the user profiles comprising the genetic information, the medical information, the therapeutic objectives, and the dietary preferences of one of the plurality of users. The genetic information, medical information, therapeutic objectives, and dietary preferences may be the same as discussed above for FIG. 5. In some embodiments, at operation 430, data may be retrieved from a food micronutrient database. The food micronutrient database may include food nutrient data for a plurality of foods and a mapping of individual micronutrients to genetic information, medical information, and therapeutic objectives. The data (e.g., nutrient data for food items, mapping of micronutrients to genetic and medical data, etc., and nutritional needs information) and the food micronutrient database may be the same as discussed above for FIG. 5.

In some embodiments, at operation 440, one or more micronutrients are identified that match the genetic information, the medical information, and/or the therapeutic objectives of the user. Identifying matching micronutrient(s) may be based on the mapping. In some embodiments, at operation 450, one or more foods are identified that provide the identified micronutrients and align with the dietary preferences of the user. Principles discussed above with respect to operations 350 and 360 may apply equally to operation 450.

In some embodiments, at operation 460, a food recommendation is sent to the user. The recommendation may be sent over a network to the user's electronic device. In some embodiments, the food recommendation may include at least one of the identified foods. Principles discussed above with respect to operation 370 may apply equally to operation 460.

In some embodiments, at operation 470, a warning for the user not to eat particular foods is outputted. The warning may be based on the genetic information, the medical information, and/or the therapeutic objectives of the user. The warning may be sent over the network together with or separate from the food recommendation. Principles discussed above with respect to operation 380 may apply equally to operation 470.

In some embodiments, at operation 480, input is received from the user indicating foods that the user has consumed. In some embodiments, the input may include a time at which the user consumed each food item. This input may be used to improve the mapping. For example, by knowing which foods the user has consumed provides important context for any feedback received because it allows the system to know what micronutrients were consumed (and thus led to improved or worsened symptoms, or led to progress towards reaching a therapeutic objective, etc.). This input may also be used to assist in making food recommendations. For example, by knowing what food the user has eaten already in a day, the system can recommend which micronutrients may be desirable for the rest of the day.

In some embodiments, fewer or more operations than are shown in FIG. 6 may be used to provide personalized food recommendations. For example, operation 470 and/or operation 480 may be omitted. As another example, an operation associated with receiving feedback may be included (as discussed above). The order of the operations may differ from what is shown in FIG. 6.

Figure 7:
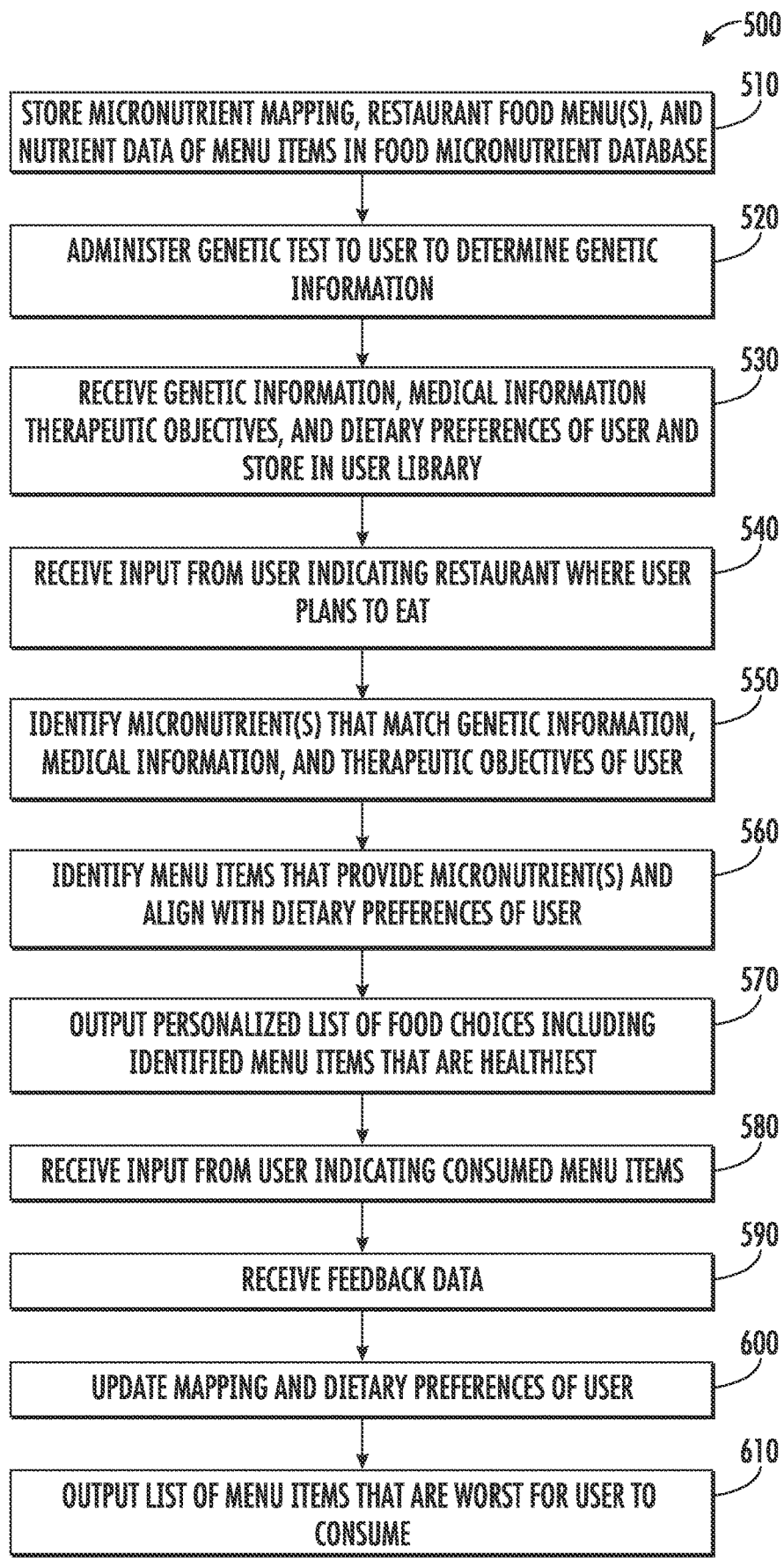
FIG. 7 shows a process flow for providing genetically personalized food recommendations according to some embodiments

FIG. 7 illustrates a method 500 of providing genetically personalized food recommendations in the context of eating at a restaurant. In some embodiments, at operation 510, a micronutrient mapping, one or more restaurant food menus, and nutrient data of the menu items on the food menus are stored in a food micronutrient database. The food micronutrient database may be accessible through an electronic device. The micronutrient mapping may be a mapping of individual micronutrients to genetic information, medical information, and/or therapeutic objectives. In some embodiments, the mapping may include genetic modifiers information about how different genes, genotypes, and genomes react to each micronutrient and combination of micronutrients.

In some embodiments, restaurants may make their menus available for the database. For example, a restaurant may send its food menu as well as the nutrient data for each of the menu items on the food menu to the database for storage. The nutrient data may include proximates data, inorganics data, micronutrients data, vitamin fractions data, fatty acid compositions data, and bioactive compounds data.

In some embodiments, at operation 520, a genetic test is administered to a user to determine genetic information (e.g., genes, genome, genotype, SNP, etc.). The genetic test may be administered by the user or by a healthcare provider. This step may be skipped if the user already knows the user's genetic information. In some embodiments, at operation 530, genetic information, medical information, therapeutic objectives, and/or dietary preferences of the user are received and stored in a user library. The user library may be coupled with the food micronutrient database. The genetic information, medical information, therapeutic objectives, and dietary preferences may be the same as discussed above for FIG. 5.

In some embodiments, at operation 540, input is received from the user indicating the restaurant where the user plans to eat. For example, the user may enter input through a software application indicating where the user plans to eat. In some embodiments, the user may type into a field the restaurant where the user plans to eat. In some embodiments, the user may select the restaurant from a list of choices. The list may be limited to the restaurants for which the food menu (with associated nutrient data for menu items) is stored in the database. In some embodiments, the list may include other restaurants. When a restaurant is selected often enough or by enough users, the restaurant may be contacted seeking its nutrient data to improve the database. After the restaurant has been selected, the system may consult the food menu from that restaurant in making recommendations.

In some embodiments, at operation 550, one or more micronutrients are identified that match the genetic information, the medical information, and/or the therapeutic objectives of the user. Identifying matching micronutrient(s) may be based on the mapping. In some embodiments, at operation 560, one or more menu items from the selected restaurant's food menu are identified that provide the identified micronutrients and align with the dietary preferences of the user. Principles discussed above with respect to operations 350 and 360 may apply equally to operation 560.

In some embodiments, at operation 570, a personalized list of food choices is outputted to the user. The personalized list of food choices includes the identified menu items that are the healthiest for the user based on the genetic information, the medical information, the therapeutic objectives, and/or the dietary preferences of the user.

In some embodiments, at operation 580, input is received from the user indicating the menu items that the user consumed. Principles discussed above with respect to operation 480 may apply equally to operation 580. In some embodiments, at operation 590, feedback data is received. In some embodiments, the feedback data comprises feedback about an effectiveness of the consumed menu items in improving the medical information. In some embodiments, the feedback data comprises feedback about an effectiveness of the consumed menu items in making progress on reaching therapeutic objectives. In some embodiments, the feedback data comprises subjective feedback data about how the user enjoyed the consumed menu items.

In some embodiments, at operation 600, the mapping and/or dietary preferences of the user may be updated. For example, the mapping may be updated based on any feedback about the effectiveness of the consumed menu items with respect to particular genetic information, medical information, and/or therapeutic objectives. Updating the mapping may follow the process discussed with respect to FIGS. 1-4. The dietary preferences of the user may be updated based on the subjective feedback about how the user enjoyed the consumed menu items. For example, if the user did not like the menu item, the system will not recommend it again. In some embodiments, the system will also not recommend similar meals if the user did not like the menu item.

In some embodiments, at operation 610, a list of menu items that are worst for the user to consume based on the genetic information, the medical information, and/or the therapeutic objectives of the user is outputted. In some embodiments, the list is accompanied with a warning not to consume particular menu items. Principles discussed above with respect to operation 380 may apply equally to operation 610.

In some embodiments, fewer or more operations than are shown in FIG. 7 may be used to provide personalized food recommendations. For example, operation 520 and/or operation 610 may be omitted. The order of the operations may differ from what is shown in FIG. 7.

Figure 8:
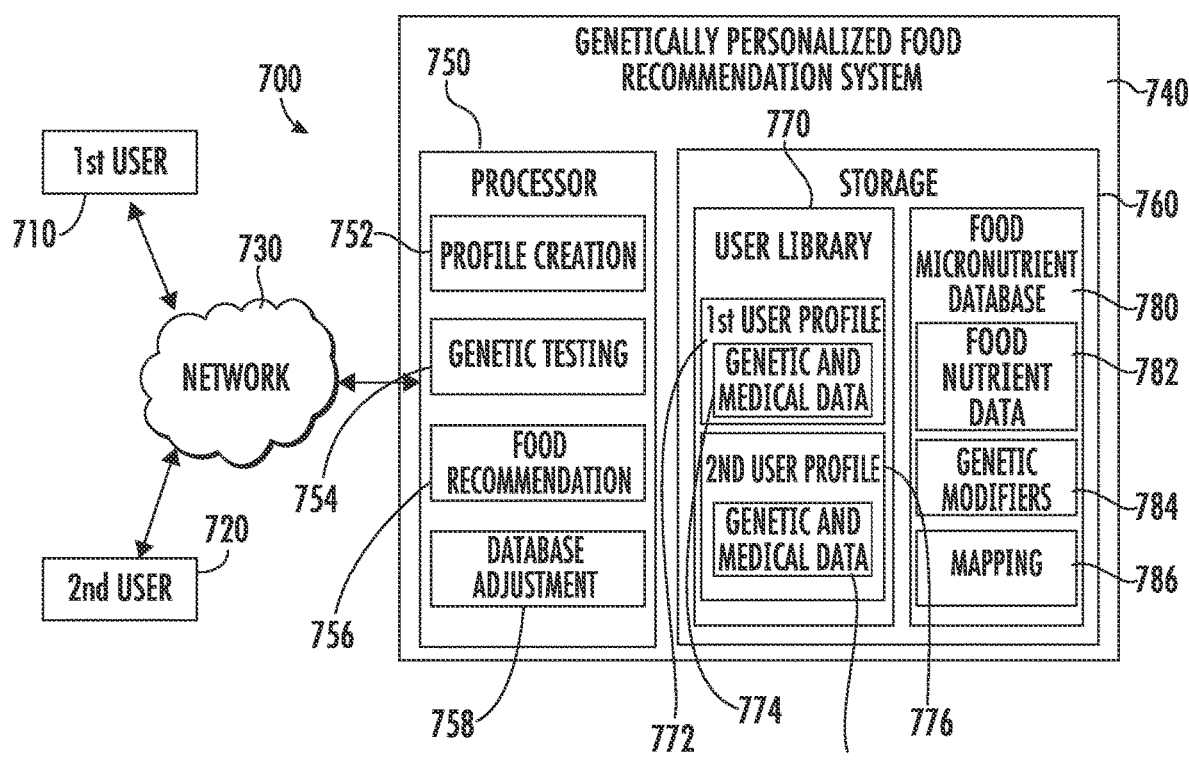
FIG. 8 shows a genetically personalized food recommendation system according to some embodiments.

In some embodiments, as shown, for example, in FIG. 8, a system 700 comprises a number of electronic devices (e.g., a first user's electronic device 710 and a second user's electronic device 720), a network 730, and a genetically personalized food recommendation system 740. FIG. 8 illustrates just one implementation of a genetically personalized food recommendation system 740. The genetically personalized food recommendation system 740 disclosed herein may be implemented with a computer or other electronic device. For example, as shown in FIG. 8, the genetically personalized food recommendation system 740 may comprise a processor 750 and a storage 760. In some embodiments, the processor 750 is communicatively coupled to network 730 and the storage 760. The electronic devices 710, 720 are also communicatively coupled to network 730, allowing users (such as first and second user) to access the genetically personalized food recommendation system 740.

In some embodiments, the storage 760 may comprise a user library 770 with a plurality of user profiles including a first user profile 772 and a second user profile 776. The user profiles 772, 776 may correspond to each user of the food recommendation system 740 disclosed above (e.g., the first user and the second user associated with electronic devices 710, 720). Each user profile 772, 776 may contain personal information such as a name or other identifier, as well as the genetic data regarding the user's genome, genotype, SNPs or other genetic data. For example, first user profile 772 includes the genetic data 774 of the first user and second user profile 776 includes the genetic data 778 of the second user. The user profiles 772, 776 may also contain medical information, personal dietary preferences, and/or personal health objectives of the user, such as weight loss, muscle gain, improved energy, etc as part of data 774. In some embodiments, users may enter or update this data via their electronic devices 710, 720. In some embodiments, other users (e.g., healthcare providers) may gain access to another user's profile to enter or update genetic and medical data. For example, the first user's healthcare provider may gain access to first user profile 772 to update genetic and other medical data 774.

The storage 760 may also comprise a food micronutrient database 780. The food micronutrient database 780 is an important aspect of the food recommendation system 740. In some embodiments, the food micronutrient database 780 includes food nutrient data 782 for a plurality of foods. For example, the food nutrient data 782 may include data regarding different foods and dishes from all over the world. In some embodiments, these foods and dishes include home-cooked dishes or recipes, food products sold at a grocery store, ingredients for a recipe, menu items from restaurants, or any other foods or dishes. In some embodiments, certain foods may be grouped together for comparison against each other. For example, each menu item on a restaurant's food menu may be grouped together so that a best option for a user eating at the restaurant may be determined and recommended.

Detailed information regarding each of these foods and dishes may be included in the food micronutrient database 780. For example, individual data 782 for each food may include, but is not limited to proximates (such as water, protein, fat, carbohydrate, energy, starch, oligosaccharides, total sugars, glucose, galactose, fructose, sucrose, maltose, lactose, alcohol, NSP/AOAC fibre, saturated fatty acids, total n-6 polyunsaturated fatty acids, total n-3 polyunsaturated fatty acids, cis-monounsaturated fatty acids, monounsaturated fatty acids, cis-polyunsaturated fatty acids, polyunsaturated fatty acids, saturated fatty acids, etc.), inorganics (such as sodium, potassium, calcium, magnesium, phosphorus, iron, copper, zinc, chloride, manganese, selenium, iodine, etc.), micronutrients (such as retinol, carotene, total retinal equivalent, vitamin D, vitamin E, vitamin K1, thiamin, riboflavin, niacin, tryptophan/60, vitamin B6, vitamin B12, folate/folic acid, pantothenate, biotin, vitamin C, etc.), vitamin fractions including retinol equivalents (such as all-trans retinol, 13-cis-retinol, dehydronretinol and retinaldehyde), carotene equivalents (such as alpha-carotene, beta-carotene, etc.), lutein, lycopene, vitamin D (such as cholecalciferol and 25-hydroxy-vitamin D3), and vitamin E equivalents (such as alpha-, beta-, gamma-, and delta-tocopherol and alpha-, beta-, gamma-, and delta-tocotrienols), fatty acid compositions including phytosterol (such as beta-sitosterol, brassicasterol, campesterol, delta-5-avenasterol, delta-7-avenasterol, delta-7-stigmastenol, stigmasterol) and organic acid (such as citric acid and malic acid), and bioactive compounds (such as total polyphenols, phytosterols, sulfur compounds, and carotenoids).

In addition to the detailed information regarding the nutrients found in each food, the food micronutrient database 780 also includes information about genetic modifiers 784, which explain how different genes, genotypes, and genomes react to each of these nutrients and combinations of nutrients, whether that be increased or decreased absorption, increased or decreased ability to process the nutrients in a healthy manner, allergic reactions, immune system reactions, etc. This information discloses how nutrient requirements are affected by genetic modifiers. Thus, the food micronutrient database provides a key ability to understand how each food will affect the user based on the user's unique genome and genotypes.

In some embodiments, food micronutrient database 780 may also include a mapping 786 that maps individual micronutrients to genetic information, medical information (e.g., symptoms, conditions), therapeutic objectives, and combinations of these attributes. For example, mapping 786 may be the mapping 200 discussed above. In some embodiments, information about genetic modifiers 784 is part of mapping 786 rather than a separate component.

As shown above, the food micronutrient database 780 may be stored in a storage 760 accessible to the processor 750. In some embodiments, the processor 750 of the food recommendation system 740 is configured to analyze the nutritional information (including food nutrient data 782, genetic modifiers 784, and/or mapping 786) of the food micronutrient database 780 in light of the genetic data (and/or the medical information and therapeutic objectives) of the user to make recommendations to the user, and to communicate the results of this analysis to the user. Thus, the processor 750 is configured to access the information within the storage 760 and communicate with users of the food recommendation system through network 730, as shown in FIG. 8.

In some embodiments, the processor 750 comprises a number of modules to perform various actions. For example, the processor 750 may comprise a profile creation module 752, a genetic testing module 754, a food recommendation module 756, and/or a database adjustment module 758. The modules may work together. The profile creation module 752 may assist a new user creating a profile from their electronic device. For example, the processor 750 may create a user profile (e.g., first user profile 772 or second user profile 776) within the user library 770 by communicating with the user to obtain the necessary information. As part of this module, the processor 750 may be configured to receive the genetic information, the medical information, the therapeutic objectives, and the dietary preferences of the user. This process may be repeated for multiple users (e.g., each time a new user begins using the genetically personalized food recommendation system 740. For example, first user may create a profile with the first user's electronic device 710. As the first user enters data on electronic device 710, electronic device 710 may transmit the data over network 730 to genetically personalized food recommendation system 740. Processor 750 (through its profile creation module 752) may receive the data, create a new user profile (i.e., first user profile 772), and store the data 774 in the first user profile 772.

Additionally, the processor 750 (through its genetic testing module 754) may store genetic tests results in the user's profile in user library 770. This may be done by receiving the genetic test results directly from the user if the user already has the results from a past genetic test, or by helping the user to obtain genetic testing. Alternatively, the food recommendation system 740 may receive the genetic data from a laboratory, medical professional, or other entity that has conducted a genetic test on the user. The genetic testing module 754 may assist a user in determining genetic data. For example, the processor may send instructions to a user's electronic device (first user's electronic device 710) on how to use a genetic testing kit. In some embodiments, the user enters results of the genetic test onto the electronic device 710, which is then transmitted to genetically personalized food recommendation system 740. Processor 750 (through its genetic testing module 754) may then add the results of the genetic testing to the user's profile. The genetic test may be used to identify specific genes, genotypes, or SNPs of the user that are relevant to nutrition. In some embodiments, the genetic testing kit may send results directly to genetically personalized food recommendation system 740 over network 730. The genetic testing module 754 may operate as part of profile creation module 752 or it may be used later on after a profile has already been created. The genetic data of the user is stored within the user's profile and is accessible by the processor 750 for whenever the user requests a food recommendation.

The processor 750 (through its food recommendation module 756) may also provide food recommendations to the user by accessing the genetic data (and/or the medical information, therapeutic objectives, and dietary preferences) of the user, analyzing information found in the food micronutrient database 780 in light of the genetic data and/or the medical information, therapeutic objectives, and dietary preferences) of the user, and communicating the results of the analysis to the user, as discussed in more detail both above and below. For example, the food recommendation module 756 may be configured to analyze the genetic data, medical data, medical history, and personal therapeutic objectives of the user stored in a user profile (e.g., first user profile 772) using the food micronutrient database 780 to determine the nutritional needs of the user, and recommend a food based on the nutritional needs of the user. Food recommendation module 756 may follow the processes discussed above with respect to FIGS. 1-7.

Database adjustment module 758 may operate to update the food micronutrient database 780 to improve accuracy and personalization of the system 740. In some embodiments, after the user has consumed food (whether it be the recommended food or some other food), processor 750 (through its database adjustment module 758) may receive input from the user on what food was consumed and feedback from the user regarding the effect of the consumed food. The input and the feedback may be received via the user's electronic device (e.g., first user's electronic device 710) over network 730. In some embodiments, the user may respond to a question as to whether the user followed the food recommendation. If the user selects yes, then the user may provide feedback on the results. If the user selects no, the system may ask whether other food was consumed and what that food was. The user may then provide feedback on the results of that consumed food. The feedback may also be received via another user, such as the first user's healthcare provider. The database adjustment module 758 is configured to adjust the food micronutrient database 780 based on the feedback from the user and the genetic data, medical data, and therapeutic objectives of the user stored in the user profile. Database adjustment module 758 may follow the processes discussed above with respect to FIGS. 1-7.

In one implementation of the food recommendation system 740 disclosed herein, the processor 750 is configured to receive a food recommendation request from one of the plurality of users through the network 730. Processor 750 may be configured to retrieve the genetic information, the medical information, the therapeutic objectives, and the dietary preferences of that user from the user library 770 and data (e.g., food nutrient data, 782, genetic modifiers 784, and/or mapping 786) from the food micronutrient database 780. Processor 750 may identify one or more micronutrients that match the genetic information, the medical information, and the therapeutic objectives of that user based on the mapping. Processor 750 may identify a food (or multiple foods) that provides the one or more micronutrients and aligns with the dietary preferences of that user. Processor 750 may send a food recommendation comprising the food (or foods) to that user through the network 730.

In one implementation of the food recommendation system 740 disclosed herein, the processor 750 is configured to store a food micronutrient database 780, receive the genetic data of a user, store the genetic data in a user profile (e.g., first user profile 772 storing genetic data 774), receive a request for a food recommendation, retrieve information from the food micronutrient database 780 based on the parameters of the food recommendation request, and provide a recommendation regarding the user's food choices based on the information from the food micronutrient database 780 and the genetic data (e.g., genetic data 774) of the user.

The genetic data (e.g., genetic data 774) may be analyzed to determine the nutritional needs of the recipient. In some implementations of the food recommendation system disclosed herein, the genetic data is analyzed by a life science professional who is familiar with genetic data and understands what nutritional needs this data expresses. For example, experts in fields such as nutraceuticals, pharmacokinetics, pharmaceuticals, nutrition, nutritional science, nutrigenomics, biomedical sciences, food data sciences, and statistics may work together to review the genetic data and determine which nutrients can help improve the health of the recipient. In other implementations, this analysis may be automated. For example, the food micronutrient database 780 may link each gene with variations on typical nutritional needs (e.g., through mapping 786). Additionally, the food micronutrient database 780 may indicate nutritional needs for specific combinations of genes. For example, a first individual may have a specific first gene and a specific second gene. The food micronutrient database 780 may suggest a specific amount of a nutrient to provide what the first individual needs. A second individual may have the same first gene as the first individual, but a second gene different from the first individual. In some cases, the food micronutrient database 780 may suggest the same nutrient in the same amount. However, in other cases, the specific combination of the first gene with the second gene may necessitate suggesting a different amount of the same nutrient, or a different nutrient altogether. Thus, the food micronutrient database 780 is configured to take into account all of the genetic data in determining the nutritional needs of the recipient and making food recommendations. The processor 750 may be configured to analyze the data from the food micronutrient database 7880 in light of the genetic data of the user. Thus, the food micronutrient database 780 may be used by an automated process or may be used or referenced by experts, as discussed above.

The processor 750 is also configured to receive a request for a food recommendation from the user. A food recommendation request may ask for general information about what types of food are healthy for the user to consume. For example, the user may want to know on a general level what types of foods to avoid. In some instances, the user may be especially prone to weight gain when consuming carbs, and this information could be provided to the user in response to a general food recommendation request. The food recommendation request may also include a specific food which the user desires to eat and ask for information regarding the health implications of consuming that food. The system 740 could respond with a go-ahead, indicating that the food would not have negative health effects, a conditioned approval, indicating that the food is fine, but that only a limited amount would be appropriate, or a warning that the food would cause more serious unwanted health effects and that the user should not consume that food. Other responses are also considered and possible. As discussed above, the food recommendation request may also indicate that the user is at a specific restaurant and ask which dish on the menu or on a narrowed list of menu items is best. The food recommendation request may ask for a recommendation of a meal, dish, or other meal product that is based on user preference, genetic data, and/or ingredient availability at a specific restaurant. Essentially, the food recommendation request may ask for any information regarding food and food choices that the system 740 is capable of providing.

In response to the food recommendation request, the processor 750 may be configured to retrieve data from the food micronutrient database 780 and from the user's profile in user library 770. The data retrieved may include nutrient data 782 regarding specific types of food, effects of different genes on nutritional needs (e.g., information on genetic modifiers 784, mapping 786), and genetic data of the user (e.g., genetic data 774), among other data. Once the data has been retrieved, the processor 750 may be configured to analyze the retrieved data to form food recommendations. For example, the processor 750 may be configured to make comparisons of the nutrient data of different foods, analyze the effects of specific genes on sensitivity to different foods, and/or recognize, based on the user's genetic data, as well as the other food that has been selected or consumed, which foods are best for the health of the user at that specific time. The processor 750 is configured to provide a recommendation regarding food choices based on the analysis of the data from the food micronutrient database 780 and the genetic data of the individual.

In some implementations of the food recommendation system 780, an organization that provides food or beverages may upload the nutrient data 782 for their products into the food micronutrient database. Thus, once a user creates a profile and uploads their genetic data, the user may be able to get specific recommendations for which of the organization's foods and beverages would best match the needs of the user, as detailed above. The user may also request a meal or dish from a specific restaurant to match the user's genetic data and food preference. In some implementations, the specific restaurant may have a list of available ingredients and the food recommendation system may suggest a meal, dish, or other meal product based on ingredient availability, user preference, and/or the genetic data of the user.

In some embodiments, a genetically personalized food recommendation system includes a processor communicatively coupled to a network and a storage communicatively coupled to the processor. In some embodiments, the storage includes a user library and a food micronutrient database. In some embodiments, the user library includes a plurality of user profiles including a first user profile and a second user profile. In some embodiments, each of the user profiles includes personal data of a user. The personal data may include genetic data of the user, personal health objectives of the user, and dietary preferences of the user.

In some embodiments, the processor is configured to store a food micronutrient database, wherein the food micronutrient database comprises food nutrient data regarding the nutrients within different foods and genetic modifiers regarding how the food nutrient data is modified by the presence of different genes. In some embodiments, the processor is configured to receive the genetic data of the user and store the genetic data of the user in the user profile associated with the user, receive a food recommendation request from the user through the network, wherein the food recommendation request indicates information needed, retrieve data from the food micronutrient database and the user profile of the user, analyze the data from the food micronutrient database and the genetic data of the user to create a food recommendation for the user, and provide the food recommendation to the user through the network.

In some embodiments, the processor is configured to receive the genetic data from the user. In some embodiments, the processor is configured to receive the genetic data from a laboratory or medical professional based on a genetic test conducted on the user. In some embodiments, the food recommendation request asks for general information about what types of food are healthy for the user. In some embodiments, the food recommendation request asks for the health implications of consuming a specific food. In some embodiments, the food recommendation request asks for a comparison of the health implications of consuming at least two different foods. In some embodiments, the food recommendation request asks for a recommendation of a dish from a specific restaurant menu. In some embodiments, the food recommendation request asks for a recommendation of a meal based on at least one of preferences of the user, genetic data of the user, and ingredient availability at a specific restaurant.

Figure 9:
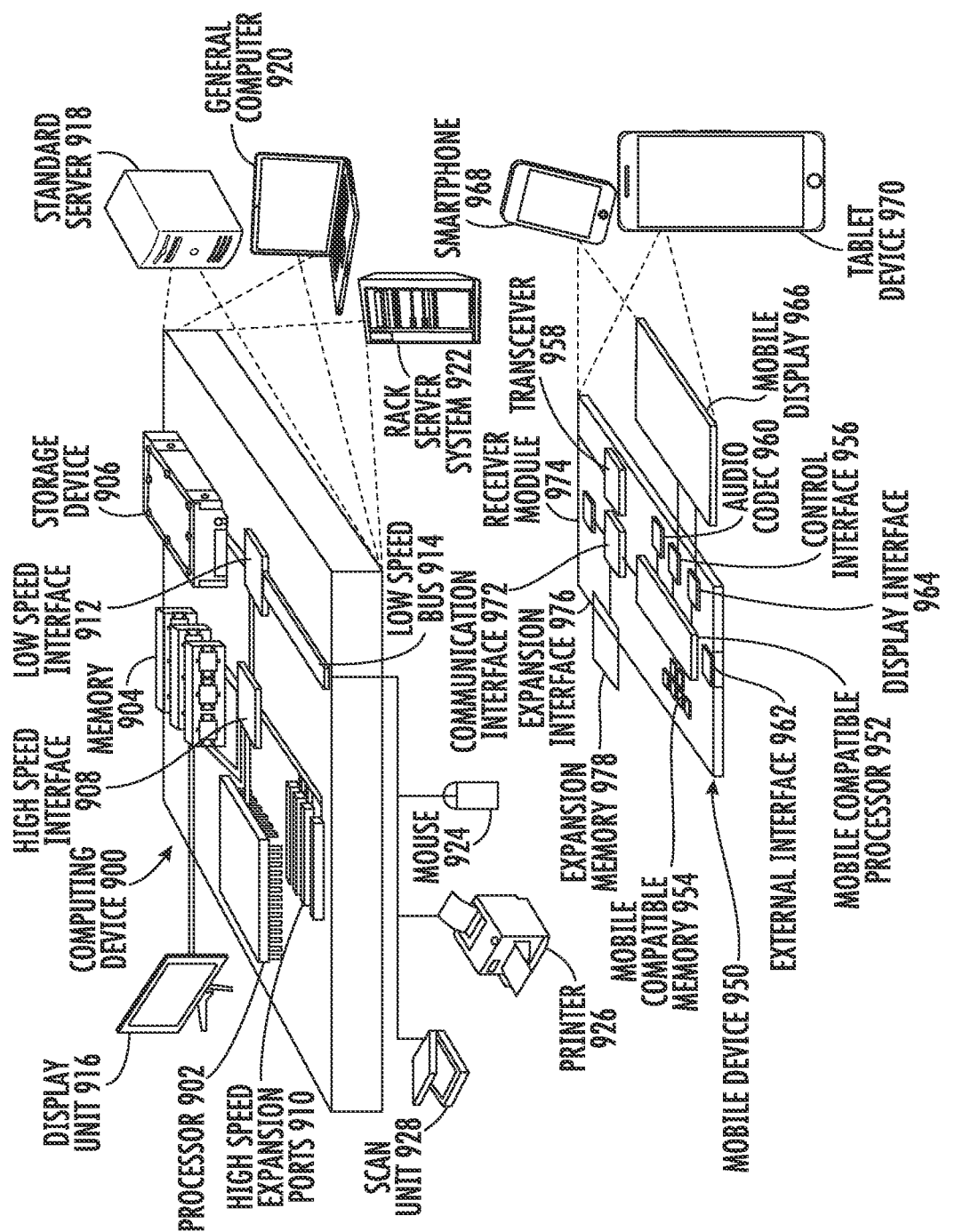
FIG. 9 shows a schematic diagram of computing devices that can be used to perform or implement the embodiments disclosed herein.

As discussed above, the genetically personalized food recommendation systems and methods disclosed herein may be partially or fully implemented with a computer or some other electronic device. For example, the food recommendation system may be available as an app on a phone or a webpage on a computer. Thus, the user may access the food recommendation system through a phone, computer, or other device. As one example, FIG. 9 is a schematic diagram of specific computing device 900 and a specific mobile computing device 950 that can be used to perform and/or implement any of the embodiments disclosed herein.

The specific computing device 900 may represent various forms of digital computers, such as laptops, desktops, workstations, personal digital assistants, servers, blade servers, mainframes, and/or other appropriate computers. The specific mobile computing device 950 may represent various forms of mobile devices, such as smartphones, camera phones, personal digital assistants, cellular telephones, and other similar mobile devices. The components shown here, their connections, couples, and relationships, and their functions, are meant to be exemplary only, and are not meant to limit the embodiments described and/or claimed, according to one embodiment.

The specific computing device 900 may include a processor 902, a memory 904, a storage device 906, a high-speed interface 908 coupled to the memory 904 and a plurality of high-speed expansion ports 910, and a low-speed interface 912 coupled to a low-speed bus 914 and a storage device 906. In one embodiment, each of the components heretofore may be inter-coupled using various buses, and may be mounted on a common motherboard and/or in other manners as appropriate. The processor 902 may process instructions for execution in the specific computing device 900, including instructions stored in the memory 904 and/or on the storage device 906 to display a graphical information for a GUI on an external input/output device, such as a display unit 916 coupled to the high-speed interface 908, according to one embodiment.

In other embodiments, multiple processors and/or multiple buses may be used, as appropriate, along with multiple memories and/or types of memory. Also, a plurality of specific computing devices 900 may be coupled with, with each device providing portions of the necessary operations (e.g., as a server bank, a group of blade servers, and/or a multi-processor system).

The memory 904 may be coupled to the specific computing device 900. In one embodiment, the memory 904 may be a volatile memory. In another embodiment, the memory 904 may be a non-volatile memory. The memory 904 may also be another form of computer-readable medium, such as a magnetic and/or an optical disk. The storage device 906 may be capable of providing mass storage for the specific computing device 900. In one embodiment, the storage device 906 may be a floppy disk device, a hard disk device, an optical disk device, a tape device, a flash memory and/or other similar solid state memory device. In another embodiment, the storage device 906 may be an array of the devices in a computer-readable medium previously mentioned heretofore, including devices in a storage area network and/or other configurations.

A computer program may be comprised of instructions that, when executed, perform one or more methods, such as those described above. The instructions may be stored in the memory 904, the storage device 906, a memory coupled to the processor 902, and/or a propagated signal.

The high-speed interface 908 may manage bandwidth-intensive operations for the specific computing device 900, while the low-speed interface 912 may manage lower bandwidth-intensive operations. Such allocation of functions is exemplary only. In one embodiment, the high-speed interface 908 may be coupled to the memory 904, the display unit 916 (e.g., through a graphics processor and/or an accelerator), and to the plurality of high-speed expansion ports 910, which may accept various expansion cards.

In the embodiment, the low-speed interface 912 may be coupled to the storage device 906 and the low-speed bus 914. The low-speed bus 914 may be comprised of a wired and/or wireless communication port (e.g., a Universal Serial Bus ("USB"), a Bluetooth® port, an Ethernet port, and/or a wireless Ethernet port). The low-speed bus 914 may also be coupled to the scan unit 928, a printer 926, a keyboard, a mouse 924, and a networking device (e.g., a switch and/or a router) through a network adapter.

The specific computing device 900 may be implemented in a number of different forms, as shown in the figure. In one embodiment, the specific computing device 900 may be implemented as a standard server 918 and/or a group of such servers. In another embodiment, the specific computing device 900 may be implemented as part of a rack server system 922. In yet another embodiment, the specific computing device 900 may be implemented as a general computer 920 such as a laptop or desktop computer. Alternatively, a component from the specific computing device 900 may be combined with another component in a specific mobile computing device 950. In one or more embodiments, an entire system may be made up of a plurality of specific computing device 900 and/or a plurality of specific computing device 900 coupled to a plurality of specific mobile computing device 950.

In one embodiment, the specific mobile computing device 950 may include a mobile compatible processor 952, a mobile compatible memory 954, and an input/output device such as a mobile display 966, a communication interface 972, and a transceiver 958, among other components. The specific mobile computing device 950 may also be provided with a storage device, such as a microdrive or other device, to provide additional storage. In one embodiment, the components indicated heretofore are inter-coupled using various buses, and several of the components may be mounted on a common motherboard.

The mobile compatible processor 952 may execute instructions in the specific mobile computing device 950, including instructions stored in the mobile compatible memory 954. The mobile compatible processor 952 may be implemented as a chipset of chips that include separate and multiple analog and digital processors. The mobile compatible processor 952 may provide, for example, for coordination of the other components of the specific mobile computing device 950, such as control of individual interfaces, applications run by the specific mobile computing device 950, and wireless communication by the specific mobile computing device 950.

The mobile compatible processor 952 may communicate with a individual through the control interface 956 and the display interface 964 coupled to a mobile display 966. In one embodiment, the mobile display 966 may be a Thin-Film-Transistor Liquid Crystal Display ("TFT LCD"), an Organic Light Emitting Diode ("OLED") display, and another appropriate display technology. The display interface 964 may comprise appropriate circuitry for driving the mobile display 966 to present graphical and other information to a individual. The control interface 956 may receive commands from a individual and convert them for submission to the mobile compatible processor 952.

In addition, an external interface 962 may be in communication with the mobile compatible processor 952, so as to enable near area communication of the specific mobile computing device 950 with other devices. External interface 962 may provide, for example, for wired communication in some embodiments, or for wireless communication in other embodiments, and multiple interfaces may also be used.

The mobile compatible memory 954 may be coupled to the specific mobile computing device 950. The mobile compatible memory 954 may be implemented as a volatile memory and a non-volatile memory. The expansion memory 978 may also be coupled to the specific mobile computing device 950 through the expansion interface 976, which may comprise, for example, a Single In Line Memory Module ("SIMM") card interface. The expansion memory 978 may provide extra storage space for the specific mobile computing device 950, or may also store an application or other information for the specific mobile computing device 950.

Specifically, the expansion memory 978 may comprise instructions to carry out the processes described above. The expansion memory 978 may also comprise secure information. For example, the expansion memory 978 may be provided as a security module for the specific mobile computing device 950, and may be programmed with instructions that permit secure use of the specific mobile computing device 950. In addition, a secure application may be provided on the SIMM card, along with additional information, such as placing identifying information on the SIMM card in a non-hackable manner.

The mobile compatible memory may include a volatile memory (e.g., a flash memory) and a non-volatile memory (e.g., a non-volatile random-access memory ("NVRAM")). In one embodiment, a computer program comprises a set of instructions that, when executed, perform one or more methods. The set of instructions may be stored on the mobile compatible memory 954, the expansion memory 978, a memory coupled to the mobile compatible processor 952, and a propagated signal that may be received, for example, over the transceiver 958 and/or the external interface 962.

The specific mobile computing device 950 may communicate wirelessly through the communication interface 972, which may be comprised of a digital signal processing circuitry. The communication interface 972 may provide for communications using various modes and/or protocols, such as a Global System for Mobile Communications ("GSM") protocol, a Short Message Service ("SMS") protocol, an Enhanced Messaging System ("EMS") protocol, a Multi-media Messaging Service ("MIMS") protocol, a Code Division Multiple Access ("CDMA") protocol, Time Division Multiple Access ("TDMA") protocol, a Personal Digital Cellular ("PDC") protocol, a Wideband Code Division Multiple Access ("WCDMA") protocol, a CDMA2000 protocol, and a General Packet Radio Service ("GPRS") protocol.

Such communication may occur, for example, through the transceiver 958 (e.g., radio-frequency transceiver). In addition, short-range communication may occur, such as using a Bluetooth®, Wi-Fi, and/or other such transceiver. In addition, a GPS ("Global Positioning System") receiver module 974 may provide additional navigation-related and location-related wireless data to the specific mobile computing device 950, which may be used as appropriate by a software application running on the specific mobile computing device 950.

The specific mobile computing device 950 may also communicate audibly using an audio codec 960, which may receive spoken information from a individual and convert it to usable digital information. The audio codec 960 may likewise generate audible sound for a individual, such as through a speaker (e.g., in a handset smartphone of the specific mobile computing device 950). Such a sound may comprise a sound from a voice telephone call, a recorded sound (e.g., a voice message, a music files, etc.) and may also include a sound generated by an application operating on the specific mobile computing device 950.

The specific mobile computing device 950 may be implemented in a number of different forms, as shown in the figure. In one embodiment, the specific mobile computing device 950 may be implemented as a smartphone 968. In another embodiment, the specific mobile computing device 950 may be implemented as a personal digital assistant ("PDA"). In yet another embodiment, the specific mobile computing device, 950 may be implemented as a tablet device 970.

Various embodiments of the systems and techniques described here can be realized in a digital electronic circuitry, an integrated circuitry, a specially designed application specific integrated circuits ("ASICs"), a piece of computer hardware, a firmware, a software application, and a combination thereof. These various embodiments can include embodiment in one or more computer programs that are executable and/or interpretable on a programmable system including one programmable processor, which may be special or general purpose, coupled to receive data and instructions from, and to transmit data and instructions to, a storage system, one input device, and at least one output device.

These computer programs (also known as programs, software, software applications, and/or code) comprise machine-readable instructions for a programmable processor, and can be implemented in a high-level procedural and/or object-oriented programming language, and/or in assembly/machine language. As used herein, the terms "machine-readable medium" and/or "computer-readable medium" refers to any computer program product, apparatus and/or device (e.g., magnetic discs, optical disks, memory, and/or Programmable Logic Devices ("PLDs")) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a individual, the systems and techniques described here may be implemented on a computing device having a display device (e.g., a cathode ray tube ("CRT") and/or liquid crystal ("LCD") monitor) for displaying information to the individual and a keyboard and a mouse by which the individual can provide input to the computer. Other kinds of devices can be used to provide for interaction with a individual as well; for example, feedback provided to the individual can be any form of sensory feedback (e.g., visual feedback, auditory feedback, and/or tactile feedback) and input from the individual can be received in any form, including acoustic, speech, and/or tactile input.

The systems and techniques described here may be implemented in a computing system that includes a back-end component (e.g., as a data server), a middleware component (e.g., an application server), a front end component (e.g., a client computer having a graphical individual interface, and/or a Web browser through which a individual can interact with an embodiment of the systems and techniques described here), and a combination thereof. The components of the system may also be coupled through a communication network.

The communication network may include a local area network ("LAN") and a wide area network ("WAN") (e.g., the Internet). The computing system can include a client and a server. In one embodiment, the client and the server are remote from each other and interact through the communication network.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

Where the above examples, embodiments and implementations reference examples, it should be understood by those of ordinary skill in the art that other use case, execution environments, and data structures could be intermixed or substituted with those provided. In places where the description above refers to particular embodiments of a personalized food recommendation system or method, it should be readily apparent that a number of modifications may be made without departing from the spirit thereof and that these embodiments and implementations may be applied to other personalized food recommendation systems and methods as well. Accordingly, the disclosed subject matter is intended to embrace all such alterations, modifications and variations that fall within the spirit and scope of the disclosure and the knowledge of one of ordinary skill in the art.

The concepts disclosed herein are not limited to the specific examples shown herein. It should be readily apparent that a number of modifications may be made without departing from the spirit thereof and that these implementations may be applied to other implementations disclosed or undisclosed. The presently disclosed methods and systems are, therefore, to be considered in all respects as illustrative and not restrictive.

What is claimed is:

1. A method of providing genetically personalized food recommendations, the method comprising:
storing, in a food micronutrient database accessible through an electronic device, a mapping of genetic information to individual micronutrients, wherein the mapping identifies the individual micronutrients that are a match for each piece of genetic information and indicates a specific amount of the identified individual micronutrients for each piece of genetic information;
storing, in the food micronutrient database, food nutrient data for a plurality of foods;
receiving genetic information of a user;
storing, in a user library coupled with the food micronutrient database, the genetic information of the user;
receiving a food recommendation request from the user through a software application on the electronic device;
identifying one or more micronutrients that match the genetic information of the user based on the mapping;
identifying food items from the plurality of foods that provide the specific amount of the one or more micronutrients indicated in the mapping for the genetic information of the user; and
outputting to the user a personalized list of food items comprising the identified food items that are healthiest options for the user based on the genetic information of the user.

2. The method of claim 1, further comprising receiving dietary preferences of the user, wherein the personalized list of food items only includes the identified food items that align with the dietary preferences of the user.

3. The method of claim 1, further comprising administering a genetic test to the user to determine the genetic information of the user.

4. The method of claim 1, wherein the plurality of foods comprises menu items from one or more restaurants, recipe ingredients of a home-cooked meal, and food items for sale in a grocery store.

5. The method of claim 1, wherein the mapping comprises a mapping of genetic information and medical information to individual micronutrients, and wherein the method further comprises:
receiving medical information of the user;
storing, in the user library, the medical information of the user; and
identifying one or more micronutrients that match the genetic information and medical information of the user based on the mapping.

6. The method of claim 1, wherein the mapping comprises a mapping of genetic information and therapeutic objectives to individual micronutrients, and wherein the method further comprises:
receiving therapeutic objectives of the user;
storing, in the user library, the therapeutic objectives of the user; and
identifying one or more micronutrients that match the genetic information and therapeutic objectives of the user based on the mapping.

7. A method of providing genetically personalized food recommendations, the method comprising:
storing, in a food micronutrient database, food nutrient data for a plurality of foods and a mapping of genetic information to individual micronutrients;
receiving genetic information of a user;
storing, in a user library, the genetic information of the user;
identifying one or more micronutrients for the user based on the genetic information and the mapping;
analyzing the food nutrient data of the plurality of foods to identify one or more foods of the plurality of foods that will provide the identified one or more micronutrients; and
outputting a food recommendation to the user that comprises food selected from the identified one or more foods.

8. The method of claim 7, wherein the food recommendation comprises a food plan for a period of time.

9. The method of claim 8, wherein the period of time is at least one week.

10. The method of claim 7, wherein the food recommendation comprises a food plan for one meal.

11. The method of claim 7, wherein the food recommendation comprises a single food item.

12. The method of claim 7, wherein the mapping indicates a specific amount of the individual micronutrients for each piece of genetic information.

13. The method of claim 7, wherein the mapping comprises a mapping of genetic information, medical information, and therapeutic objectives to individual micronutrients, and wherein the method further comprises:
receiving medical information and therapeutic objectives of the user;
storing, in the user library, the medical information and therapeutic objectives of the user; and
identifying one or more micronutrients for the user based on the genetic information, the medical information, and the therapeutic objectives of the user and the mapping.

14. A genetically personalized food recommendation system comprising:
a processor communicatively coupled to a network and configured to receive genetic information of a plurality of users through the network; and
a storage communicatively coupled to the processor, the storage comprising a user library and a food micronutrient database,
wherein the user library comprises a plurality of user profiles corresponding to the plurality of users, each of the user profiles comprising the genetic information of one of the plurality of users,
wherein the food micronutrient database comprises food nutrient data for a plurality of foods and a mapping of genetic information to individual micronutrients, and
wherein the processor is configured to:
receive a food recommendation request from one of the plurality of users through the network;
retrieve information regarding the genetic information of the one of the plurality of users from the user library and data from the food micronutrient database;
identify one or more micronutrients that match the genetic information of the one of the plurality of users based on the mapping;
identify at least one of the plurality of foods that provides the one or more micronutrients; and
send a food recommendation comprising the at least one of the plurality of foods to the one of the plurality of users through the network.

15. The system of claim 14, wherein the processor is configured to receive the genetic information of the plurality of users through the network directly from one or more genetic testing kits.

16. The system of claim 14, wherein the food recommendation comprises a food plan for a period of time.

17. The system of claim 16, wherein the period of time is at least one week.

18. The system of claim 14, wherein the food recommendation comprises a food plan for one meal.

19. The system of claim 14, wherein the mapping indicates a specific amount of the individual micronutrients for each piece of genetic information.

20. The system of claim 14, wherein the mapping comprises a mapping of genetic information, medical information, and therapeutic objectives to individual micronutrients, and wherein the processor is further configured to:
   receive medical information and therapeutic objectives of the plurality of users; and
   identify one or more micronutrients that match the genetic information, the medical information, and the therapeutic objectives of the one of the plurality of users based on the mapping.

* * * * *